US011517620B2

(12) United States Patent
Sakaguchi

(10) Patent No.: US 11,517,620 B2
(45) Date of Patent: Dec. 6, 2022

(54) ADJUVANT COMPOSITION, AND VACCINE COMPOSITION AND DRUG KIT EACH CONTAINING THE SAME

(71) Applicant: TERUMO KABUSHIKI KAISHA, Tokyo (JP)

(72) Inventor: Naoki Sakaguchi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 455 days.

(21) Appl. No.: 16/497,866

(22) PCT Filed: Mar. 28, 2018

(86) PCT No.: PCT/JP2018/012904
§ 371 (c)(1),
(2) Date: Sep. 26, 2019

(87) PCT Pub. No.: WO2018/181542
PCT Pub. Date: Oct. 4, 2018

(65) Prior Publication Data
US 2020/0023059 A1    Jan. 23, 2020

(30) Foreign Application Priority Data

Mar. 29, 2017  (JP) .............................. JP2017-066142

(51) Int. Cl.
| | | |
|---|---|---|
| *A61K 39/39* | (2006.01) | |
| *A61P 37/04* | (2006.01) | |
| *A61K 31/7088* | (2006.01) | |
| *A61K 39/395* | (2006.01) | |

(52) U.S. Cl.
CPC .......... *A61K 39/39* (2013.01); *A61K 31/7088* (2013.01); *A61K 39/395* (2013.01); *A61P 37/04* (2018.01)

(58) Field of Classification Search
CPC .. A61K 39/39; A61K 31/7088; A61K 39/395; A61K 39/00; A61P 37/04; A61P 35/00; A61P 37/02
See application file for complete search history.

(56) References Cited

U.S. PATENT DOCUMENTS

| | | | | |
|---|---|---|---|---|
| 9,248,192 B2* | 2/2016 | Sakaguchi | ............ | A61K 9/1075 |
| 10,179,169 B2* | 1/2019 | Sakaguchi | ............. | A61K 47/12 |
| 11,000,586 B2* | 5/2021 | Sakaguchi | ............. | A61K 9/107 |
| 2009/0117132 A1 | 5/2009 | Readett et al. | | |
| 2013/0323320 A1* | 12/2013 | Sakaguchi | ............. | A61K 38/00 424/502 |
| 2015/0374815 A1* | 12/2015 | Kishimoto | ........... | A61K 9/0019 424/186.1 |
| 2016/0130345 A1* | 5/2016 | Fotin-Mleczek | ....... | A61P 31/10 424/172.1 |
| 2016/0271246 A1 | 9/2016 | Sakaguchi | | |
| 2018/0000085 A1 | 1/2018 | Bravo-altamirano et al. | | |
| 2021/0030867 A1* | 2/2021 | Sakaguchi | .............. | A61P 37/04 |
| 2021/0145750 A1* | 5/2021 | Sakaguchi | ............. | A61K 47/24 |

FOREIGN PATENT DOCUMENTS

| | | | |
|---|---|---|---|
| JP | 2009500412 A | 1/2009 | |
| WO | 2015036792 A1 | 3/2015 | |
| WO | 2015079952 A1 | 6/2015 | |
| WO | WO-2015079952 A1 * | 6/2015 | ............. A61K 39/39 |
| WO | 2016089873 A1 | 6/2016 | |
| WO | 2016109310 A1 | 7/2016 | |

OTHER PUBLICATIONS

Lewis AL, Chaft J, Girotra M, Fischer GW. Immune checkpoint inhibitors: a narrative review of considerations for the anaesthesiologist. Br J Anaesth. Mar. 2020;124(3):251-260 (Year: 2020).*
Yin P, Liu X, Mansfield AS, et al. CpG-induced antitumor immunity requires IL-12 in expansion of effector cells and down-regulation of PD-1. Oncotarget. 2016;7(43):70223-70231. doi:10.18632/oncotarget. 11833 (Year: 2016).*
National Institute of Cancer, Apr. 29, 2010, pp. 1-2 (Year: 2010).*
Vogelstein et al. Nature Medicine, 2004, 10(8): 789-799 (Year: 2004).*
Adjiri A. DNA Mutations May Not Be the Cause of Cancer. Oncol Ther. 2017;5(1):85-101. doi: 10.1007/s40487-017-0047-1. Epub May 15, 2017. PMID: 28680959; PMCID: PMC5488117. (Year: 2017).*
Office Action (Notice of Reasons for Refusal) dated Nov. 9, 2021, by the Japanese Patent Office in corresponding Japanese Patent Application No. 2019-510015 and an English Translation of the Office Action. (10 pages).
The extended European Search Report dated Dec. 8, 2020, by the European Patent Office in corresponding European Patent Application No. 18774982.5-1110. (10 pages).
Aruga, A. et al., "Long-term Vaccination with Multiple Peptides Derived from Cancer-Testis Antigens Can Maintain a Specific T-cell Response and Achieve Disease Stability in Advanced Biliary Tract Cancer", Clin Cancer Res, 19(8) pp. 2224-2231, Apr. 15, 2013.
International Search Report (PCT/ISA/210) dated Jun. 19, 2018, by the Japan Patent Office as the International Searching Authority for International Application No. PCT/JP2018/012904.
Mangsbo, S.M. et al., "Enhanced Tumor Eradication by Combining CTLA-4 or PD-1 Blockade With CpG Therapy", J. Immunotherapy, vol. 33, No. 3, pp. 225-235, Apr. 2010.

(Continued)

*Primary Examiner* — Hong Sang
*Assistant Examiner* — Sung Min Yoon
(74) *Attorney, Agent, or Firm* — Buchanan Ingersoll & Rooney PC

(57) ABSTRACT

A combination of drugs having a higher antitumor effect is provided. There is provided an adjuvant composition containing a pH sensitive carrier and a natural immunity-activating substance, the adjuvant composition being used to be administered in combination with an immune checkpoint inhibitor.

4 Claims, 4 Drawing Sheets

Specification includes a Sequence Listing.

(56) References Cited

OTHER PUBLICATIONS

Written Opinion (PCT/ISA/237) dated Jun. 19, 2018, by the Japan Patent Office as the International Searching Authority for International Application No. PCT/JP2018/012904.

* cited by examiner

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial
<220> FEATURE:
<223> OTHER INFORMATION: ODN2395

<400> SEQUENCE: 1
tcgtcgtttt cggcgcgcgc cg                                              22
```

ADJUVANT COMPOSITION, AND VACCINE COMPOSITION AND DRUG KIT EACH CONTAINING THE SAME

TECHNICAL FIELD

The present invention relates an adjuvant composition and a vaccine composition containing the same.

BACKGROUND ART

In recent years, attention has been paid to immunotherapy in which an immune system is applied to treatment of diseases. In particular, cancer immunotherapy in which cancer is a target is receiving high expectations, and implementation of highly effective cancer immunotherapy has been demanded.

The function of the immune system is expressed via two types of mechanisms, that is, humoral immunity and cell-mediated immunity. It is found out that, since the cell-mediated immunity has a capability to damage and kill or eliminate cancer cells, the cell-mediated immunity plays an important role in cancer immunotherapy. Of cells constituting the cell-mediated immunity, cytotoxic T cells (hereinafter, also simply referred to as CTL) play a main role of damaging and killing cancer cells. Therefore, induction of a lot of CTLs becomes a necessary factor for highly effective cancer immunotherapy.

The induction of CTL is typically developed as follows. That is, an endogenous antigen such as a protein produced in virus-infected cells or cancer cells is ubiquitinated and then decomposed to a peptide by a proteasome. The decomposed peptide is bound to major histocompatibility complex (MHC) class I molecules, the obtained complex is presented to CD8 positive T cells on surfaces of antigen presenting cells, and the CD8 positive T cells are activated. Then, the activated CD8 positive T cells are differentiated into CTL.

However, since antigen presentation to the MHC class I molecules is a process occurring with respect to the endogenous antigen, antigen presentation does not occur with respect to an exogenous antigen present outside cells. Incidentally, the exogenous antigen is incorporated into an antigen presenting cell by endocytosis, digested in the endosome by a proteolytic enzyme, and decomposed into peptide fragments. The peptide fragments are presented to MHC class II molecules and used in production of an antibody. Therefore, it is well known that induction of CTL using an exogenous antigen is difficult.

In this regard, recently, cross-presentation in which CTL is actively induced using an exogenous antigen has been studied so much.

The exogenous antigen, as described above, is decomposed in the endosomes in the antigen presenting cells and is not used in antigen presentation to the MHC class I molecules. In the cross-presentation, the exogenous antigen is delivered to cytosol in cells, the exogenous antigen acts like an endogenous antigen, and thus the exogenous antigen is bound to the MHC class I molecules to perform antigen presentation. According to this, even in the case of the exogenous antigen, CTL can be induced.

Further, a substance having stimuli that activate natural immunity (hereinafter, also simply referred to as natural immunity-activating substance) induces maturation with respect to antigen presenting cells and enhances production of costimulatory molecules or MHC class I molecules. According to this, the antigen presenting cells can be induced to the form capable of inducing CTL. For this reason, it is expected that a lot of CTLs are induced by combining a technique of delivering an exogenous antigen to cytosol with the natural immunity-activating substance.

For example, WO 2015/079952 A discloses that an adjuvant composition, which is obtained by combining a pH sensitive carrier capable of delivering an antigen to cytosol through the membrane disruptive function promoting effect and a substance stimulating natural immunity, generates induction of a lot of CTLs.

Further, since CTL plays a role of damaging and killing a cell serving as a target, it has been reported that induction of a lot of CTLs leads to a highly effective cancer immunotherapy (for example, Clin Cancer Res 2013 19(8) 2224-31).

Meanwhile, cancer immunotherapy in which two drugs are combined while enhancement in antitumor effect by combining drugs is expected, using different immune systems is also under review. For example, in Mangsbo S M, et al., J Immunother 2010; 33(3): 225-35, it is described that the survival period of a tumor-bearing mouse is lengthened by administration of a combination of a short-chain DNA comprising a CpG motif that is a Toll-like receptor agonist and an anti-PD-1 antibody that is an immune checkpoint inhibitor.

SUMMARY OF INVENTION

Use in combination of drugs each having a different action mechanism in immunotherapy is considered to be effective. However, even if drugs each having a different action mechanism are used in combination, enhancement in antitumor effect is not always obtainable, so that a combination of drugs having a higher antitumor effect has been demanded.

Therefore, an object of the present invention is to provide a combination of drugs having a higher antitumor effect.

The present inventors have found that a particularly high antitumor effect is obtainable by using a combination of an adjuvant composition, which has a pH sensitive carrier added with a natural immunity-activating substance, and an immune checkpoint inhibitor, as a drug inducing a CTL, thereby completing the present invention.

Preferred embodiments of the present invention are as follows.

(1) An adjuvant composition containing a pH sensitive carrier and a natural immunity-activating substance, the adjuvant composition being used to be administered in combination with an immune checkpoint inhibitor.

(2) The adjuvant composition described in (1), in which the adjuvant composition is administered before the immune checkpoint inhibitor is administered.

(3) The adjuvant composition described in (1) or (2), in which the immune checkpoint inhibitor is at least one selected from the group consisting of an anti-PD-1 antibody, an anti-PD-L1 antibody, an anti-PD-L2 antibody, and an anti-CTLA-4 antibody.

(4) The adjuvant composition described in any one of (1) to (3), in which the pH sensitive carrier contains a pH sensitive compound and an amphipathic substance, the pH sensitive compound is at least one selected from the group consisting of deoxycholic acid, cholic acid, ursodeoxycholic acid, chenodeoxycholic acid, hyodeoxycholic acid, higher-bile acid, glycodeoxycholic acid, glycyrrhizic acid, glycyrrhetinic acid, and salts thereof, and the amphipathic substance is at least one selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil, and α-tocopherol.

Incidentally, in the present specification, the "number of carbon atoms" of the amphipathic substance means the number of carbon atoms of a fatty acid component (acyl group) constituting the hydrophobic moiety of the amphipathic substance. In a case where two or more acyl groups exist, the "number of carbon atoms" does not indicate the total number but indicates the number of carbon atoms of one acyl group.

(5) The adjuvant composition described in (4), in which the adjuvant composition develops a membrane disruptive function promoting effect.

(6) The adjuvant composition described in any one of (1) to (5), in which the natural immunity-activating substance is an oligonucleotide comprising a CpG motif.

(7) A vaccine composition containing the adjuvant composition described in any one of (1) to (6) and an antigen.

(8) A drug kit including a combination of an adjuvant composition, which contains a pH sensitive carrier and a natural immunity-activating substance, and an immune checkpoint inhibitor.

(9) The drug kit described in (8), in which the immune checkpoint inhibitor is administered after the adjuvant composition is administered.

(10) The drug kit described in (8) or (9), in which the drug kit is a drug kit for the treatment or prevention of cancer.

(11) The drug kit described in any one of (8) to (10), in which the immune checkpoint inhibitor is at least one selected from the group consisting of an anti-PD-1 antibody, an anti-PD-L1 antibody, an anti-PD-L2 antibody, and an anti-CTLA-4 antibody.

(12) The drug kit described in any one of (8) to (11), in which the pH sensitive carrier contains a pH sensitive compound and an amphipathic substance, the pH sensitive compound is at least one selected from the group consisting of deoxycholic acid, cholic acid, ursodeoxycholic acid, chenodeoxycholicacid, hyodeoxycholicacid, higherbile acid, glycodeoxycholic acid, glycyrrhizic acid, glycyrrhetinic acid, and salts thereof, and the amphipathic substance is at least one selected from the group consisting of a phosphatidyicholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil, and α-tocopherol.

(13) The drug kit described in (12), in which the adjuvant composition develops a membrane disruptive function promoting effect.

(14) The drug kit described in any one of (8) to (13), in which the natural immunity-activating substance is an oligonucleotide comprising a CpG motif.

(15) A method for treating or preventing a disease including administering an effective amount of an immune checkpoint inhibitor to a subject requiring treatment or prevention after administering an effective amount of a vaccine composition containing an adjuvant composition, which contains a pH sensitive carrier and a natural immunity-activating substance, and an antigen.

(16) The method described in (15), in which the disease is a cancer.

BRIEF DESCRIPTION OF DRAWINGS

FIG. 3(A) shows the result of a group administered with ovalbumin (hereinafter, also simply referred to as OVA) and an oligonucleotide comprising a CpG motif, FIG. 3(B) shows the result of a group administered with OVA, an oligonucleotide comprising a CpG motif, and a pH sensitive carrier, and FIG. 3(C) shows the result of a group administered with OVA and a pH sensitive carrier.

FIG. 4(A) shows the results obtained by observing the antitumor effect of the adjuvant composition and the combination use effect of the adjuvant composition and the immune checkpoint inhibitor, and FIG. 4(B) shows the results of verification of the details of the combination use effect.

FIG. 5(A) shows mice of Group 3, FIG. 5(B) shows mice of Group 6, and FIG. 5(C) shows mice of Group 7.

DESCRIPTION OF EMBODIMENTS

Figure 1:
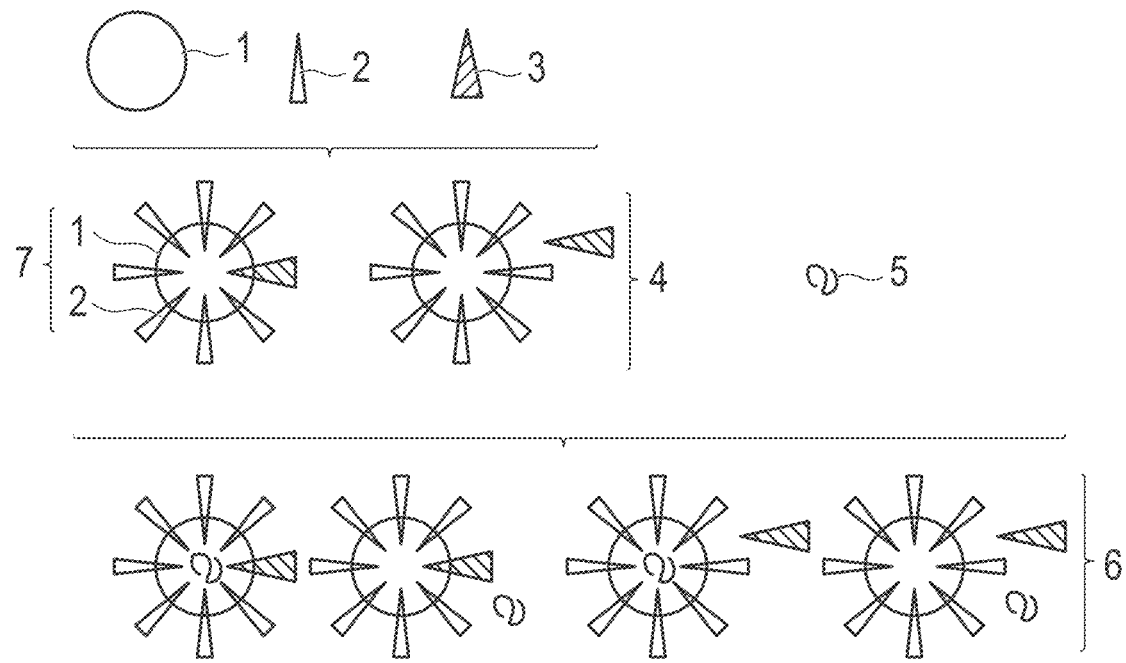
FIG. 1 is a schematic view of an adjuvant composition and a vaccine composition containing the adjuvant composition.

Hereinafter, embodiments of the present invention will be described. Incidentally, the present invention is not limited only to the following embodiments.

In the present specification, "X to Y" indicating the range means "X or more and Y or less" including X and Y. In addition, in the present specification, unless otherwise stated, the operations and the measurements of physical properties are conducted under the conditions of room temperature (20° C. to 25° C.)/relative humidity of 40% RH to 50% RH.

Hereinafter, an adjuvant composition and a vaccine composition will be described with reference to the drawings; however, the technical scope of the present invention is to be defined based on the description in the claims and is not limited only to the following embodiments. Incidentally, the dimensional ratios in the drawings are exaggerated for convenience of explanation, and may be different from the actual ratios.

According to FIG. 1, an adjuvant composition 4 contains an amphipathic substance 1, a pH sensitive compound 2, and a natural immunity-activating substance 3. Further, in FIG. 1, a pH sensitive carrier 7 is configured by the amphipathic substance 1 and the pH sensitive compound 2.

As shown in FIG. 1, according to an embodiment, the natural immunity-activating substance 3 associates with a hydrophobic moiety constituting the amphipathic substance 1 together with the pH sensitive compound 2. In this case, the adjuvant composition 4 can be also said to be an adjuvant complex. In addition, according to another embodiment, the natural immunity-activating substance 3 exists independently from a pH sensitive carrier containing the amphipathic substance 1 and the pH sensitive compound 2.

Further, a vaccine composition 6 contains the adjuvant composition 4 and an antigen 5. As shown in FIG. 1, the antigen 5 may be embraced in, or may exist independently from, the adjuvant composition 4 according to the above-described two embodiments. Among these, particularly, the vaccine composition 6 in which the antigen 5 is embraced in the adjuvant complex 4 can be also said to be a vaccine complex.

In the present specification, the "adjuvant composition" means a composition containing a pH sensitive carrier and a natural immunity-activating substance, and the form thereof is not particularly limited. That is, the "adjuvant composition" may be a composition obtained by mixing a pH sensitive carrier and a natural immunity-activating substance or may be a composition in which a natural immunity-activating substance is supported on or embraced in a pH sensitive carrier (adjuvant complex), and both of these types of compositions are collectively referred to as "adjuvant composition" in the present specification.

Further, in the present specification, the "vaccine composition" means a composition containing an adjuvant composition and an antigen, and the form thereof is not particularly limited. That is, the "vaccine composition" may be a composition in which two or more selected from the group consisting of the constituents of an adjuvant composition and an antigen are mixed together, or may be a composition in which an antigen is supported on or embraced in an adjuvant complex (vaccine complex), and both of these types of compositions are collectively referred to as "vaccine composition" in the present specification.

Figure 3A:
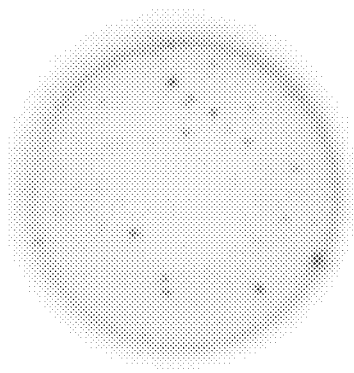
FIGS. 3(A)-3(C) are views showing the induction evaluation of CTL by an ELIspot method.
Figure 3B:
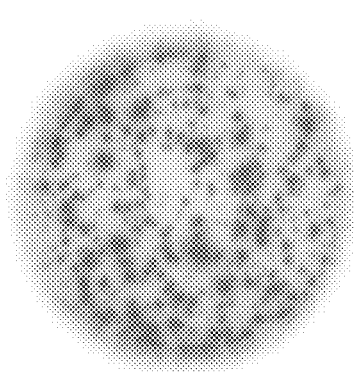

By the vaccine composition 6, induction of CTL is increased (FIG. 3(B)). The reason for this has not yet been elucidated, but the reason is inferred to be as follows.

Figure 2:
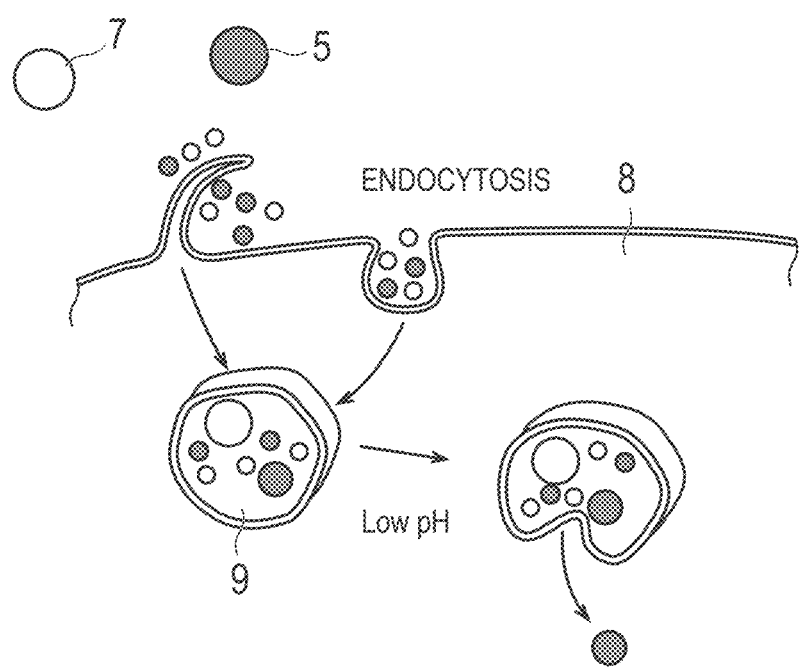
FIG. 2 is a schematic view showing a mechanism that is assumed in which induction of CTL is increased by the vaccine composition.

First, by the natural immunity-activating substance, an antigen presenting cell (a dendritic cell in FIG. 2) is matured (not shown). Further, the antigen 5 and the pH sensitive carrier 7 are captured into a dendritic cell 8 by endocytosis and then migrate into an endosome 9. By the pH sensitive carrier, the antigen is delivered from the endosome to the cytosol and is subjected to processing of the dendritic cell. Thereafter, the fragmented antigen is bound to the MHC class I molecule to present the antigen on the cell surface. In the matured dendritic cell, since production of the costimulatory molecule or the MHC class I molecule is enhanced, induction of CTL is considered to increase. The maturation of the dendritic cell and the delivery of the antigen to the cytosol are not necessary to occur at the same time, so that the natural immunity-activating substance and the pH sensitive carrier may not be necessarily in the form of the complex or may exist independently in the adjuvant composition. Further, in the vaccine composition, the antigen may exist independently from the natural immunity-activating substance and the pH sensitive carrier.

Incidentally, the mechanism of delivering the antigen from the inside of the endosome to the cytosol by the pH sensitive carrier will be described later.

<Adjuvant Composition>

The adjuvant composition contains a pH sensitive carrier (hereinafter, simply referred to as "carrier," "associated product," or "complex" in some cases) and a natural immunity-activating substance. According to the adjuvant composition of the present invention, a high antitumor effect can be obtained.

[pH Sensitive Carrier]

The pH sensitive carrier is sensitive to pH and has a function of being able to transport an antigen in cells to cytosol when pH is brought into an acidic range. The pH sensitive carrier contains a pH sensitive compound and an amphipathic substance.

Hereinafter, the pH sensitive carrier, which contains a pH sensitive compound and an amphipathic substance, will be described in detail.

(Structure of pH Sensitive Carrier)

It is considered that the pH sensitive carrier is formed by association between the pH sensitive compound and the amphipathic substance at a physiological pH or more. More specifically, it is considered that the pH sensitive compound associates with the hydrophobic moiety of the amphipathic substance to form the pH sensitive carrier. Incidentally, the form of association of the pH sensitive carrier is an inferred one, and the pH sensitive carrier is not limited to the form of association.

(Membrane Disruptive Function Promoting Effect)

It is preferable that the pH sensitive carrier has a membrane disruptive function.

The term "membrane disruptive function" means a function of causing leakage in a leaching test. Herein, the leaching test in the present specification is a test in which liposomes (dispersion) including an aqueous solution containing a quenching substance and a fluorescent substance, and an evaluation sample dispersion are added to an aqueous solution whose pH is adjusted to a predetermined level, followed by incubating the aqueous solution at 37° C. for 90 minutes or 30 minutes and measuring the fluorescence of the aqueous solution. According to this method, an amount of a fluorescent substance dissolved or leached out from the liposomes can be measured, from which the liposome membrane disruptive function of the pH sensitive carrier can be confirmed. Incidentally, the leaching test will be described in more detail in Examples described later.

Further, the expression "to develop a membrane disruptive function promoting effect" means to satisfy both of requirements (1) and (2): (1) in the leaching test, a leakage at a predetermined pH that is less than a physiological pH increases compared to a leakage at the physiological pH and the amount of increase is larger than the amount of increase in a case where the pH sensitive compound alone is subjected to the test; and (2) in the leaching test at a predetermined pH less than the physiological pH, a leakage when a pH sensitive compound and an amphipathic substance form a pH sensitive carrier is more than the sum of a leakage of the pH sensitive compound alone and a leakage of the amphipathic substance alone. More specifically, to develop a membrane disruptive function promoting effect means that, in the leaching test at a pH of 7.4 and at a pH of 5.0 or 4.5, a leakage Lc of the pH sensitive carrier, a leakage La of the pH sensitive compound alone, and a leakage Lb of the amphipathic substance alone satisfy both the following relations. That is, the above (1) is represented by the following Formula (1) and the above (2) is represented by the following Formula (2). Incidentally, in the following formulas, leakages at a pH of 7.4 are, respectively, denoted by $Lc_{7.4}$, $La_{7.4}$, and $Lb_{7.4}$, and leakages at a pH of 5.0 or 4.5 are, respectively, denoted by $Lc_x$, $La_x$, and $Lbx$.

[Math. 1]

$$\Delta = (Lc_x - Lc_{7.4}) - (La_x - La_{7.4}) > 0 \quad \text{Formula(1)}$$

$$\Delta' = Lc_x - (La_x + Lb_x) > 0 \quad \text{Formula(2)}$$

In the above Formula (1), $\Delta$ may exceed 0 and is preferably 5 or more, more preferably 10 or more, and further preferably 30 or more. Incidentally, a larger $\Delta$ is preferred, and the upper limit thereof is not particularly limited, but is generally less than 100. In addition, in the above Formula (2), $\Delta'$ may exceed 0 and is preferably 5 or more, more preferably 10 or more, and further preferably 15 or more. Incidentally, a larger $\Delta'$ is preferred, and the upper limit thereof is not particularly limited, but is generally less than 100.

In an embodiment of the present invention, Δ and Δ' in the above Formulas (1) and (2) are, respectively, 5 or more, and a pH sensitive carrier containing a bile acid and a lipid is preferred.

Herein, the term "physiological pH" in the present specification means a pH in a normal tissue or normal body fluid. The physiological pH is generally 7.4 and differs slightly (±0.1) depending on the normal tissue or normal body fluid. In addition, the term "a predetermined pH less than a physiological pH" may be a pH of less than 7.4, and is preferably a pH of 3.0 or more and a pH of less than 7.4, more preferably a pH of 4.0 or more and a pH of less than 7.3, and further preferably a pH of 4.5 or more and a pH of less than 7.0.

No elucidation has been made yet on the mechanism by which the pH sensitive carrier develops a membrane disruptive function promoting effect, but the following inference may be made. Incidentally, the present invention is not limited by the following inference.

It is considered that the pH sensitive carrier changes in the mode of association of the pH sensitive compound and the amphipathic substance in a case where the environment decreases in pH less than the physiological pH, and as a result, the pH sensitive carrier has a membrane disruptive function promoting effect. For example, it is inferred that in a case where a pH is less than the physiological pH in a system in which a pH sensitive carrier and a biological membrane (such as a cell membrane or a vesicle membrane) exist, the pH sensitive carrier changes in the mode of association, and after the pH sensitive carrier contacts with the biological membrane, a change in the membrane structure of the biological membrane is induced by the change. That is, the pH sensitive carrier brings about a change in the membrane structure of the biological membrane. The reason for this is that a change of pH into a weak acid range makes unstable the pH sensitive compound in the pH sensitive carrier in the structure of the carrier, with the result that the pH sensitive carrier undergoes rearrangement with the biological membrane existing in the system, thereby developing the membrane disruptive function promoting effect. Further, in other words, it is considered that the pH sensitive compound is molecules which, when a pH is changed into a weak acid range, undergo protonation and change the solubility into hydrophobic association. That is, it can be said that the hydrophobic association involving the pH sensitive compound can develop the function by responding to the weak acid environment. Incidentally, the term "membrane disruption" refers to such a change in membrane structure, and may not always involve separation or decomposition of all of the membrane constituent components. Owing to the occurrence of such "membrane disruption," the components contained inside the biological membrane (for example, endosome), for example, leach to outside (for example, cytosol) of the biological membrane.

The pH sensitive carrier is preferably one whose leakage in the leaching test is less than 20% at a pH of 7.4 and more than 20% at a pH of 4.0. Further, the leakage in the leaching test is more preferably less than 20% at a pH of 6.5 and more than 20% at a pH of 4.0. Further, in the above description, the leakage at a pH or 7.4 or pH of 6.5 is more preferably 15% or less and further preferably 10% or less. Further, the leakage at a pH of 4.0 is more preferably 40% or more and further preferably 50% or more. When the leakage of the pH sensitive carrier is set as defined above, the development of the membrane disruptive function promoting effect at a pH in a weak acid range can be better shown.

Further, the pH sensitive carrier is also able to develop a membrane fusion function promoting effect along with the membrane disruptive function promoting effect.

In the present invention, the term "membrane fusion function" means a function of causing membrane fusion in a membrane fusion test. Herein, the membrane fusion test in the present specification is a test in which a liposome (dispersion) incorporating two types of fluorescent substances in a bimolecular membrane, and an evaluation sample dispersion are added to an aqueous solution adjusted to a predetermined pH, and the resulting aqueous solution is incubated at 37° C. for 60 minutes, followed by measurement of the fluorescence of the aqueous solution. According to this method, variations in energy resonance transfer of the two types of fluorescent substances incorporated in the liposome can be measured, and thus the membrane fusion function of the pH sensitive carrier can be confirmed. Incidentally, in the membrane fusion test, the method described in [0189] to [0194] of WO 2015/079952 A (US 2016/0,271,246 A, [0307] to [0312]) is adopted.

In addition, the expression "to develop a membrane fusion function promoting effect" means that, in the membrane fusion test, a fusion rate at a predetermined pH less than a physiological pH increases compared to a fusion rate at the physiological pH and the amount of increase is larger than the amount of increase in a case where the pH sensitive compound alone is subjected to the test. More specifically, to develop a membrane fusion function promoting effect means that, in the membrane fusion test at a pH of 7.4 and at a pH of 5.0, a fusion rate Rc (%) of a pH sensitive carrier (a complex of a pH sensitive compound and an amphipathic substance) satisfies the following relation of the following Formula (3) with a fusion rate Ra (%) of the pH sensitive compound alone. Incidentally, in the following formula, the fusion rates at a pH of 7.4 are, respectively, denoted by $Rc_{7.4}$ and $Ra_{7.4}$, and the fusion rates at a pH of 5.0 are, respectively, denoted by $Rc_x$ and $Ra_z$.

[Math. 2]

$$\Delta R = (Rc_x - Rc_{7.4}) - (Ra_x - Ra_{7.4}) > 0 \qquad \text{Formula (3)}$$

In the above Formula (3), ΔR may exceed 0, and is preferably 2 or more, more preferably 5 or more, and further preferably 10 or more.

In the above Formula (3), the pH sensitive carrier is preferably a pH sensitive carrier which has ΔR of 2 or more and contains a bile acid and a lipid.

The pH sensitive carrier develops the membrane fusion function promoting effect at a pH in a weak acid range (a predetermined pH less than the physiological pH). Although the mechanism of this phenomenon is not yet elucidated, the mechanism is considered to be similar to the mechanism in the membrane disruptive function promoting effect described above. Incidentally, the present invention is not limited by the inference.

That is, it is inferred that the pH sensitive carrier of the present invention contributes to membrane fusion as a result of rearrangement with biological membranes existing in the system, through a change in the mode of association between the pH sensitive compound and the amphipathic substance, in a case where the environment decreases in pH less than the physiological pH. At this time, the membrane fusion takes place as a result of rearrangement among components having affinity for each other, and hence those components which have no or little affinity for biological membrane (such as antigen) are excluded and released from the membrane which undergoes rearrangement.

As described above, generally, the antigen is surrounded by endosome, which is one kind of biological membrane, and taken into cells (such as antigen presenting cells). After that, the pH inside the endosome is lowered by the action of a proton pump. Moreover, the endosome fuses with a lysosome containing a hydrolase, so that the antigen is decomposed (subsequently, the decomposed antigen forms a complex with MHC class II molecules, thereby being presented to CD4 positive T cells). Therefore, most of the antigen remains undelivered into the cytosol.

On the other hand, by using the pH sensitive carrier, the antigen (such as exogenous antigen) can be delivered to the cytosol. More specifically, when the antigen together with the pH sensitive carrier is surrounded by endosomes and taken into cells, similarly, an environment with a decreased pH is derived. Further, with a decrease in pH (acidification), the pH sensitive compound makes unstable the pH sensitive carrier, so that the rearrangement of membranes occurs between the endosome and the pH sensitive carrier. As a result, the membrane disruptive function (depending on cases, the membrane disruptive function which is developed along with the membrane fusion function) occurs due to the pH sensitive carrier. With this membrane disruptive function (or the membrane fusion function and the membrane disruptive function), the antigen may be delivered from the endosome to the cytosol. Incidentally, according to the above-described mechanism, it is understood that, since in principle, the antigen can be transported to the cytosol so long as it has been taken into the endosome together with the pH sensitive carrier, the form in the mixed composition of the antigen and the pH sensitive carrier may be used, or the form that the antigen is supported on or embraced in the pH sensitive carrier may be used.

(pH Sensitive Compound)

The pH sensitive compound is preferably at least one selected from the group consisting of deoxycholic acid, cholic acid, ursodeoxycholic acid, chenodeoxycholic acid, hyodeoxycholicacid, higher bile acid, glycodeoxycholic acid, glycyrrhizic acid, glycyrrhetinic acid, and salts thereof. The salts of the pH sensitive compound are not particularly limited, but examples thereof include alkali metal salts such as lithium, sodium, and potassium; alkaline earth metal salts such as magnesium, calcium, and barium; ammonium salt; and the like. These pH sensitive compounds may be used singly or in combination of two or more kinds thereof.

According to an embodiment of the present invention, the pH sensitive compound is preferably at least one selected from the group consisting of deoxycholic acid, cholic acid, ursodeoxycholic acid, chenodeoxycholic acid, hyodeoxycholic acid, glycodeoxycholic acid, glycyrrhizic acid, and salts thereof.

Further, according to another embodiment of the present invention, the pH sensitive compound is preferably at least one selected from the group consisting of deoxycholic acid, ursodeoxycholic acid, chenodeoxycholic acid, hyodeoxycholic acid, glycodeoxycholic acid, glycyrrhizic acid, and salts thereof, and more preferably at least one selected from the group consisting of deoxycholic acid, ursodeoxycholic acid, glycyrrhizic acid, and salts thereof.

The deoxycholic acid, cholic acid, ursodeoxycholic acid, chenodeoxycholic acid, hyodeoxycholic acid, higherbile acid, and glycodeoxycholic acid, which are preferably used as the pH sensitive compound, are generally called "bile acid." The bile acid has been known as a typical steroid derivative since before the 1920s and has been utilized in the field of bacteriology. The bile acid forms complexes with cholesterol, lipids and fat-soluble vitamins in the human body and has a role of supplementing absorption thereof. Moreover, because of the capability of forming complexes with lipids, proteins, and hydrophobic materials in view of physicochemical properties of the bile acid, it has been long utilized for isolation and purification of proteins and also as a solubilizer or emulsifier. In recent years, attention has been paid to the use in a preparation process of vaccine and also to as an absorption enhancer for drug through a bile acid transporter. In particular, sodium deoxycholate (also known as sodium desoxycholate) and ursodeoxycholic acid (also known as ursodesoxycholic acid) have been approved as a pharmaceutical additive capable of being injected to humans, respectively, and their superior safety performance has been recognized. Therefore, as the pH sensitive compound, deoxycholic acid, ursodeoxycholic acid, or salts thereof (for example, sodium salts) are further preferably used, and deoxycholic acid or a salt thereof (for example, a sodium salt) is particularly preferably used.

The amount of the pH sensitive compound with respect to 100 mol of the amphipathic substance is preferably 10 mol or more, more preferably 10 to 640 mol, further preferably 20 to 320 mol, and particularly preferably 20 to 160 mol.

(Amphipathic Substance)

The amphipathic substance is preferably at least one selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil, and α-tocopherol. These amphipathic substances may be used singly or in combination of two or more kinds thereof.

Incidentally, in the present specification, the "number of carbon atoms" in the amphipathic substance means the number of carbon atoms in the fatty acid component (acyl group) constituting the hydrophobic moiety of the amphipathic substance. In a case where two or more acyl groups exist, the "number of carbon atoms" does not indicate the total number but indicates the number of carbon atoms of one acyl group. For example, in the case of dilauroylphosphatidylcholine, the dilauroylphosphatidylcholine contains two lauric acid components, but the number of carbon atoms of the dilauroylphosphatidylcholine indicates the number of carbon atoms of one lauric acid component of the two lauric acid components, that is, 12. When the number of carbon atoms constituting the hydrophobic moiety of phosphatidylcholine is 10 to 12, which is an appropriate length, the amphipathic lipid has a micelle forming ability and is also easily fused to a membrane (WO 2013/180253 A, FIG. 8).

As the phosphatidylcholine having 10 to 12 carbon atoms, diacylphosphatidylcholine having a saturated acyl group is preferred, and examples thereof include didecanoylphosphatidylcholine (DDPC; 1,2-didecanoyl-sn-glycero-3-phosphatidylcholine), and dilauroylphosphatidylcholine (DLPC; 1,2-dilauroyl-sn-glycero-3-phosphatidylcholine). Among these, as the phosphatidylcholine, a naturally-derived one or a synthesized one obtained by a known method may be used, or commercially available ones can be used. When the number of carbon atoms constituting the hydrophobic moiety of the phosphatidylcholine is 10 to 12, which is an appropriate length, the amphipathic lipid has a micelle forming ability and also easily induces rearrangement of a membrane.

Examples of the polyoxyethylene sorbitan monofatty acid ester having 12 to 18 carbon atoms include polyoxyethylene sorbitan monolauric acid ester (polyoxyethylene sorbitan monolaurate), polyoxyethylene sorbitan myristic acid ester (polyoxyethylene sorbitan monomyristate), polyoxyethylene sorbitan monopalmitic acid ester (polyoxyethylene sorbitan palmitate), polyoxyethylene sorbitan monostearic acid ester (polyoxyethylene sorbitan monostearate), polyoxyethylene sorbitan monooleic acid ester (polyoxyethylene sorbitan monooleate), and the like. Although the degree of polymerization of polyoxyethylene is not particularly limited, the degree of polymerization with respect to the total of polyoxyethylene chains added to sorbitan is preferably 10 to 200, more preferably 15 to 100, and further preferably 20 to 50. As the polyoxyethylene sorbitan monofatty acid ester, a synthesized one may be used or a commercial one may be used. As a commercial product of the polyoxyethylene sorbitan monofatty acid ester, there can be preferably used, for example, those commercially sold under the designations of Tween 20 (polyoxyethylene sorbitan monolauric acid ester), Tween 40 (polyoxyethylene sorbitan monopalmitic acid ester), Tween 60 (polyoxyethylene sorbitan monostearic acid ester), and Tween 80 (polyoxyethylene sorbitan monooleic acid ester). Among these, polyoxyethylene sorbitan monofatty acid esters having 12 to 18 carbon atoms (Tween 20, Tween 40, Tween 60, and Tween 80) are preferably used.

Examples of the sorbitan fatty acid ester having 16 to 18 carbon atoms include sorbitan monofatty acid esters such as sorbitan monopalmitic acid ester (sorbitan monopalmitate), sorbitan monostearic acid ester (sorbitan monostearate), and sorbitan monooleic acid ester (sorbitan monooleate); sorbitan trifatty acid esters such as sorbitan tripalmitic acid ester (sorbitan tripalmitate), sorbitan tristearic acid ester (sorbitan tristearate), and sorbitan trioleic acid ester (sorbitan trioleate); and the like. As the sorbitan fatty acid ester, a synthesized one may be used or a commercial one may be used. As a commercial product of the sorbitan fatty acid ester, there can be preferably used, for example, those commercially sold under the designations of SPAN 40 (sorbitan palmitic acid ester), SPAN 60 (sorbitan stearic acid ester), SPAN 80 (sorbitan oleic acid ester), SPAN 65 (sorbitan tristearic acid ester), and SPAN 85 (sorbitan trioleic acid ester). Among these, SPAN 80, SPAN 65, and SPAN 85 are preferably used.

The glycerol monooleate (glyceryl monooleate), glycerol dilaurate (glyceryl dilaurate), glycerol distearate (glyceryl distearate), and glycerol dioleate (glyceryl dioleate) are acyl glycerols in which one or two molecules of a fatty acid are ester-bound to glycerin, and the sites at which the fatty acid is bound are not particularly limited. For example, with glycerol monooleate that is a monoacyl glycerol, the fatty acid may be ester-bound to at the C1 or C2 position of glycerin. Further, with glycerol dilaurate, glycerol distearate, and glycerol dioleate that are each a diacyl glycerol, the fatty acid may be ester-bound to at the C1 and C2 positions or at the C1 and C3 positions of glycerin. For example, as glycerol dilaurate, α,α'-dilaurin which is substituted at the C1 and C3 positions is preferred. As glycerol distearate or glycerol dioleate, diacyl glycerol which is substituted at the C1 and C2 positions is preferred. As these glycerol derivatives, a synthetized one may be used or a commercial one may be used.

As a polyoxyethylene castor oil, mention is made of adducts of polyoxyethylenes to castor oil. The degree of polymerization of polyoxyethylene is not particularly limited, but is preferably 3 to 200, more preferably 5 to 100, and further preferably 10 to 50. As the polyoxyethylene castor oil, a synthetized one may be used or a commercial one may be used.

As α-tocopherol, a naturally-derived one or a synthesized one obtained by a known method may be used, or commercially available ones may be used.

Among the aforementioned amphipathic substances, the amphipathic substance is preferably at least one selected from the group consisting of phosphatidylcholine having 10 to 12 carbon atoms, polyoxyethylene sorbitan monolaurate, polyoxyethylene sorbitan monooleate, sorbitan monooleate, polyoxyethylene castor oil, and α-tocopherol, more preferably at least one selected from the group consisting of dilauroylphosphatidylcholine, didecanoylphosphatidylcholine, polyoxyethylene sorbitan monolaurate, polyoxyethylene sorbitan monooleate, sorbitan monooleate, polyoxyethylene castor oil, and α-tocopherol, further preferably dilauroylphosphatidylcholine and/or didecanoylphosphatidylcholine, and particularly preferably dilauroylphosphatidylcholine.

(Combination of pH Sensitive Compound and Amphipathic Substance)

It is preferable that the pH sensitive compound is at least one selected from the group consisting of deoxycholic acid, cholic acid, ursodeoxycholic acid, chenodeoxycholic acid, hyodeoxycholic acid, higher bile acid, glycodeoxycholic acid, glycyrrhizic acid, glycyrrhetinic acid, and salts thereof, and the amphipathic substance is at least one selected from the group consisting of a phosphatidylcholine having 10 to 12 carbon atoms, a polyoxyethylene sorbitan monofatty acid ester having 12 to 18 carbon atoms, a sorbitan fatty acid ester having 16 to 18 carbon atoms, glycerol monooleate, glycerol dilaurate, glycerol distearate, glycerol dioleate, polyoxyethylene castor oil, and α-tocopherol.

The pH sensitive carrier can develop a membrane disruptive function promoting effect at a desired pH by the combination of a pH sensitive compound and an amphipathic substance. At this time, the pH at which the pH sensitive carrier commences to develop the membrane disruptive function promoting effect differs depending on the combination of a pH sensitive compound and an amphipathic substance. This is considered for the following reasons: pKa differs depending on the type of pH sensitive compound and the manner of forming association with an amphipathic substance also differs depending on the combination of a pH sensitive compound and an amphipathic substance. Therefore, when a combination of a pH sensitive compound and an amphipathic substance is appropriately changed, the proper choice of the pH at which the function can be developed is possible, thus enabling delivery to be designed in detail.

In the pH sensitive carrier, preferable combinations of pH sensitive compounds and amphipathic substances include cholic acid and DLPC, deoxycholic acid and DDPC, deoxycholic acid and DLPC, deoxycholic acid and Tween 20, deoxycholic acid and Tween 40, deoxycholic acid and Tween 60, deoxycholic acid and Tween 80, deoxycholic acid and SPAN 40, deoxycholic acid and SPAN 60, deoxycholic acid and SPAN 80, deoxycholic acid and SPAN 65, deoxycholic acid and SPAN 85, deoxycholic acid and α-tocopherol, deoxycholic acid and glycerol monooleate, deoxycholic acid and glycerol distearate, deoxycholic acid and glycerol dioleate, deoxycholic acid and glycerol dilaurate (α,α'-dilaurin), deoxycholic acid and polyoxyethylene castor oil, chenodeoxycholic acid and DLPC, hyodeoxycholic acid and DLPC, glycodeoxycholic acid and DLPC, ursodeoxycholic acid and DDPC, ursodeoxycholic acid and DLPC, ursodeoxycholic acid and Tween 20, ursodeoxycholic acid and Tween 40, ursodeoxycholic acid and Tween 60, ursodeoxycholic acid and Tween 80, ursodeoxycholic acid and SPAN 40, ursodeoxycholic acid and SPAN 60, ursodeoxycholic acid and SPAN 80, ursodeoxycholic acid and SPAN 65, ursodeoxycholic acid and SPAN 85, ursodeoxycholic acid and α-tocopherol, ursodeoxycholic acid and glycerol monooleate, ursodeoxycholic acid and glycerol distearate, ursodeoxycholic acid and glycerol dioleate, ursodeoxycholic acid and glycerol dilaurate (α,α'-dilaurin), ursodeoxycholic acid and polyoxyethylene castor oil, glycyrrhizic acid and DDPC, glycyrrhizic acid and DLPC, glycyrrhizic acid and Tween 20, glycyrrhizic acid and Tween 40, glycyrrhizic acid and Tween 60, glycyrrhizic acid and Tween 80, glycyrrhizic acid and SPAN 40, glycyrrhizic acid and SPAN 60, glycyrrhizic acid and SPAN 80, glycyrrhizic acid and SPAN 65, glycyrrhizic acid and SPAN 85, glycyrrhizic acid and α-tocopherol, glycyrrhizic acid and glycerol monooleate, glycyrrhizic acid and glycerol distearate, glycyrrhizic acid and glycerol dioleate, glycyrrhizic acid and glycerol dilaurate (α,α'-dilaurin), and glycyrrhizic acid and polyoxyethylene castor oil. In the above description, the pH sensitive compound may be a salt.

More preferably, mention is made of cholic acid and DLPC, deoxycholic acid and DDPC, deoxycholic acid and DLPC, deoxycholic acid and Tween 20, deoxycholic acid and Tween 40, deoxycholic acid and Tween 60, deoxycholic acid and Tween 80, deoxycholic acid and SPAN 40, deoxycholic acid and SPAN 65, deoxycholic acid and SPAN 80, deoxycholic acid and SPAN 85, deoxycholic acid and α-tocopherol, deoxycholic acid and glycerol monooleate, deoxycholic acid and polyoxyethylene castor oil, chenodeoxycholic acid and DLPC, hyodeoxycholic acid and DLPC, glycodeoxycholic acid and DLPC, ursodeoxycholic acid and DDPC, ursodeoxycholic acid and DLPC, ursodeoxycholic acid and Tween 40, ursodeoxycholic acid and Tween 60, ursodeoxycholic acid and Tween 80, ursodeoxycholic acid and SPAN 40, ursodeoxycholic acid and SPAN 65, ursodeoxycholic acid and SPAN 85, ursodeoxycholic acid and α-tocopherol, ursodeoxycholic acid and monoolein, ursodeoxycholic acid and polyoxyethylene castor oil, glycyrrhizic acid and DDPC, glycyrrhizic acid and DLPC, glycyrrhizic acid and Tween 40, glycyrrhizic acid and Tween 60, glycyrrhizic acid and Tween 80, glycyrrhizic acid and SPAN 40, glycyrrhizic acid and SPAN 65, glycyrrhizic acid and SPAN 85, glycyrrhizic acid and α-tocopherol, glycyrrhizic acid and glycerol monooleate, and glycyrrhizic acid and polyoxyethylene castor oil. In the above description, the pH sensitive compound may be a salt.

Particularly preferably, mention is made of deoxycholic acid and DDPC, deoxycholic acid and DLPC, deoxycholic acid and Tween 20, deoxycholic acid and Tween 80, deoxycholic acid and SPAN 80, deoxycholic acid and α-tocopherol, ursodeoxycholic acid and DDPC, ursodeoxycholic acid and DLPC, and glycyrrhizic acid and DLPC, and most preferably, mention is made of deoxycholic acid and DDPC, and deoxycholic acid and DLPC. In the above description, the pH sensitive compound may be a salt.

[Natural Immunity-Activating Substance]

The natural immunity-activating substance means a substance which is recognized by a receptor for structural pattern recognition and leads immunocompetent cells into an active state.

The natural immunity-activating substance is not particularly limited, but is preferably an agonist with respect to a Toll-like receptor.

Specific examples of the natural immunity-activating substance include, although not particularly limited, an oligonucleotide comprising a CpG motif; mineral salts such as alum; gel-type adjuvants such as aluminum hydroxide, aluminum phosphate, and calcium phosphate; immunostimulatory RNA molecules; endotoxins (lipopolysaccharide (LPS; endotoxin); monophosphoryl lipid A (MPL: registered trademark)); exotoxins (cholera toxin, *Escherichia coli* (*E. coli*) thermolabile toxin, pertussis toxin); microbial adjuvants such as muramyl dipeptide and flagellin; oil adjuvants such as incomplete Freund's adjuvant (IFA); oil adjuvants such as liquid paraffin and lanolin; biodegradable microspheres; saponins (such as QS-21 and Quil-A); nonionic block copolymers; muramyl peptide analogs; polyphosphazenes; synthetic polynucleotides (such as non-CpG synthetic polynucleotide); synthetic adjuvants such as imidazoquinoline; cationic lipids such as DOTAP, DC-Chol, and DDA; single-stranded RNA; double-stranded RNA; and the like. Among these, the natural immunity-activating substance is preferably an oligonucleotide comprising a CpG motif; mineral salts; gel-type adjuvants such as aluminum hydroxide, aluminum phosphate, and calcium phosphate; immunostimulatory RNA molecules; monophosphoryl lipid A (MPL: registered trademark)), exotoxins (cholera toxin, *Escherichia coli* (*E. coli*) thermolabile toxin, pertussis toxin); microbial adjuvants such as flagellin; saponins (such as QS-21 and Quil-A); synthetic polynucleotides (such as non-CpG synthetic polynucleotide); synthetic adjuvants such as imidazoquinoline; single-stranded RNA; double-stranded RNA; and the like, and more preferably an oligonucleotide including monophosphoryl lipid A, a CpG motif, and aluminum hydroxide, and from the viewpoint of being particularly excellent in combination use effect with the immune checkpoint inhibitor, particularly preferably an oligonucleotide comprising a CpG motif.

The natural immunity-activating substance may be used singly or in combination of two or more kinds thereof.

The content of the natural immunity-activating substance varies depending on the type of the natural immunity-activating substance to be used, but is preferably 0.0227 to 22.7 mol with respect to 100 mol of the amphipathic substance. When the content of the natural immunity-activating substance is 0.0227 mol or more, immune response can be suitably induced, which is preferable. On the other hand, when the content of the natural immunity-activating substance is 22.7 mol or less, cost can be reduced, which is preferable.

The oligonucleotide comprising a CpG motif is preferably a non-methylated CpG oligodeoxynucleotide (CpG ODN) and more preferably a non-methylated CpG oligodeoxynucleotide (CpG ODN) that is a ligand of Toll-like receptor 9 (TLR9). The oligodeoxynucleotide indicates a compound in which deoxynucleoside (deoxyadenosine (the base moiety is adenine (A)), deoxyguanosine (the base moiety is guanine (G)), thymidine (the base moiety is thymine (T)), and deoxycytidine (the base moiety is cytosine (C))) form a multimer by phosphodiester binding via phosphoric acid. A portion of phosphodiester binding of oligonucleotide may be partly or entirely subjected to phosphorothioate modification in which an oxygen atom is substituted with a sulfur atom. The phosphorothioate-modified phosphodiester binding can be called phosphorothioate binding.

The non-methylated CpG oligodeoxynucleotide (CpG ODN) is an oligodeoxynucleotide having a single or a plurality of non-methylated CpG motifs in the nucleic acid molecule (not in the 5' terminal or 3' terminal). Herein, the non-methylated CpG motif refers to cytosine (C)-guanine (G) (5'-CpG-3') dinucleotide sequence that is a dinucleotide sequence in which the 5-position of the cytosine is not methylated. In general, in eukaryotes, regarding the 5'-CpG-3' sequence, the cytosine is methylated by CG methylase, so that the appearance frequency in the genome of non-methylated 5'-CpG-3' sequence is small.

The non-methylated CpG oligodeoxynucleotide (CpG ODN) can be easily produced using a known nucleic acid synthesis method and a commercial product may be used.

The CpG ODN is preferably composed of 18 to 25 deoxynucleotides and more preferably composed of 20 to 22 deoxynucleotides.

As the CpG ODN, CpG ODNs of Class A (also referred to as type D), Class B (also referred to as type K), and Class C are exemplified.

CpG ODN of Class A indicates CpG ODN that is a palindrome sequence including one or more non-methylated CpG sequences and is composed of a portion having phosphodiester binding as a skeleton and a portion, which is a poly G sequence bound to the 5' side and/or the 3' side of the palindrome sequence (poly(G), a sequence in which two or more deoxyguanosines are connected), having phosphorothioate binding as a skeleton. Incidentally, the palindrome sequence indicates a sequence having a palindromic structure in which the sequence and the sequence of complementary strand coincide with each other.

Specific examples of the CpGODN of Class A include ODN2216, ODN2336, and ODN1585. All of these can be purchased from InvivoGen.

The CpG ODN of Class B indicates CpG ODN in which one or more non-methylated CpG sequences are included in the sequence and the skeleton is phosphorothioate binding over the oligonucleotide full length. Specific examples of the CpG ODN of Class B include ODN2006, ODN1668, and ODN1826. All of these can be purchased from InvivoGen.

The CpG ODN of type C indicates CpG ODN which is composed of the 5' side portion including one or more non-methylated CpG sequences in the sequence and the 3' side portion including a palindrome sequence having a non-methylated CpG sequence and has phosphorothioate binding as a skeleton over the oligonucleotide full length. Specific examples of CpG ODN of Class C include ODN2395 and ODN M362. Regarding ODN2395 and ODN M362, an immunostimulatory activity is significantly recognized in humans and mice. All of these can be purchased from InvivoGen.

[Aqueous Solvent]

The adjuvant composition may contain an aqueous solvent.

In a case where the adjuvant composition is an aqueous solvent, the pH sensitive carrier and the natural immunity-activating substance can form a dispersion dispersed in the aqueous solvent.

At this time, the pH sensitive carrier preferably forms a complex containing the pH sensitive compound and the amphipathic substance in the aqueous solvent. The form of this complex is not particularly limited, and the pH sensitive compound and the amphipathic substance may form a membrane or the pH sensitive compound may be partly or entirely embedded in a structure formed by the amphipathic substance via association or the like. In addition, it is preferable that the pH sensitive compound and the amphipathic substance form micelle particles (particles in which the pH sensitive compound and the amphipathic substance are associated into particulate form through hydrophobic interaction, and which are typically particles of a monomolecular membrane structure). Further, since taking-in by phagocytosis or endocytosis is actively performed for particles having a size equal to or larger than a certain size, the particle diameter of the micelle particles is preferably 10 to 200 nm and more preferably 10 to 100 nm. Incidentally, the above-described micelle particles do not include those which form lipid bimolecular membrane structure (such as liposome). Further, in the present specification, the particle diameter of the pH sensitive carrier can be measured by a dynamic light scattering method (with NanoZS90 manufactured by MALVERN Instruments Co., Ltd.).

Further, the adjuvant composition preferably forms a complex (adjuvant complex) which contains the pH sensitive carrier in the form of complex and the natural immunity-activating substance in an aqueous solvent. Although the form of the complex is not particularly limited, it is preferable that the pH sensitive substance and the amphipathic substance, which constitute the pH sensitive carrier, and the natural immunity-activating substance form micelle particles. The particle diameter of the micelle particles is preferably 10 to 200 nm and more preferably 10 to 100 nm.

Incidentally, in the aqueous solvent containing the adjuvant composition, at least one of the pH sensitive compound, the amphipathic substance, and the substance having an activity to activate natural immunity may remain in a free state without forming an associated product.

As the aqueous solvent, an aqueous solution containing a buffer, NaCl, and a sugar such as glucose and sucrose is preferred.

As the buffer, a known buffer can be appropriately used so long as it can keep the pH of the adjuvant composition equal to or more than the physiological pH, and the buffer is not particularly limited. Examples of the buffer include a phosphate buffer, a citrate buffer, a citrate-phosphate buffer, a trishydroxymethylaminomethane-HCl buffer (Tris-hydrochloride buffer), trishydroxymethylaminomethane-EDTA buffer (Tris-EDTA buffer, TE buffer), GOOD buffers such as an MES buffer (2-morpholinoethanesulfonate buffer), a TES buffer (N-tris(hydroxymethyl)methyl-2-aminoethanesulfonate buffer), an acetate buffer, an MOPS buffer (3-morpholinopropanesulfonate buffer), an MOPS-NaOH buffer, an HEPES buffer (4-(2-hydroxyethyl)-1-piperazineethanesulfonate buffer), and an HEPES-NaOH buffer, amino acid buffers such as a glycine-hydrochloride buffer, a glycine-NaOH buffer, a glycylglcyine-NaOH buffer, and a glycylglycine-KOH buffer; boric acid-based buffers such as a Tris-borate buffer, a borate-NaOH buffer, and a borate buffer; an imidazole buffer; and the like. Of these, a phosphate buffer such as a PBS (phosphate buffered saline), a citrate buffer, a citrate-phosphate buffer, a Tris-hydrochloride buffer, a Tris-EDTA buffer (TE buffer), an MES buffer, an acetate buffer, and an HEPES-NaOH buffer are preferably used. The concentration of the buffer is not particularly limited, but is preferably 0.1 to 200 mM and more preferably 1 to 100 mM. Incidentally, in the present specification, the term "concentration of the buffer" refers to the concentration (mM) of the buffer contained in the aqueous solvent.

The concentrations of NaCl and a sugar such as glucose and sucrose are not particularly limited, but are preferably 0.1 to 200 mM and more preferably 1 to 150 mM.

The concentration of the pH sensitive carrier in the adjuvant composition in the case of using the aqueous solvent is not particularly limited, but the total molar concentration of the pH sensitive compound and the amphipathic substance is preferably 0.73 µmol/L to 7.4 mmol/L, more preferably 7.3 µmol/L to 6.5 mmol/L, and further preferably 8.0 µmol/L to 4.2 mmol/L.

Further, the molar concentration of the natural immunity-activating substance in the adjuvant composition in the case of using the aqueous solvent is not particularly limited, but is preferably 0.14 nmol/L to 0.227 mmol/L, more preferably 1.4 nmol/L to 0.19 mmol/L, and further preferably 1.6 nmol/L to 0.12 mmol/L.

[Other Components]

The adjuvant composition may contain other components.

The other components are not particularly limited, but a stabilizer and the like are exemplified.

The stabilizer is not particularly limited so long as it does not adversely affect the pH sensitive carrier and the natural immunity-activating substance, and known stabilizers can be used, examples of which include saturated or unsaturated alcohols having 4 to 20 carbon atoms such as 1-octanol, 1-dodecanol, 1-hexadodecanol, and 1-eicosanol; saturated or unsaturated fatty acids having 12 to 18 carbon atoms such as lauric acid, myristic acid, palmitic acid, stearic acid, and oleic acid; alkyl esters (alkyl having 1 to 3 carbon atoms) of saturated or unsaturated fatty acids having 8 to 18 carbon atoms such as methyl caprylate (methyl octanoate), ethyl caprylate (ethyl octanoate), methyl laurate, ethyl laurate, ethyl myristate, ethyl palmitate, ethyl stearate, methyl oleate, and ethyl oleate; D(L)-amino acids such as D(L)-alanine, arginine, asparagine, aspartic acid, cysteine, glutamine, glycine, histidine, leucine, isoleucine, lysine, methionine, proline, serine, threonine, tryptophan, tyrosine, valine, phenylalanine, and glutamic acid; amino acid triglycerides such as tricaproin and tricaprylin; polyoxyethylene sorbitan trifatty acid esters having 12 to 18 carbon atoms such as polyoxyethylene sorbitan tripalmitic acid ester and polyoxyethylene sorbitan trioleic acid ester (for example, Tween 65 and Tween 85); polyoxyethylene alkyl esters having 12 to 18 carbon atoms such as polyoxyethylene lauric acid ester, polyoxyethylene myristic acid ester, polyoxyethylene palmitic acid ester, and polyoxyethylene stearic acid ester (for example, PEG20 stearyl ether and PEG23 lauryl ether); polyoxyalkylene hardened castor oil (for example, PEG10 hardened castor oil, PEG40 hardened castor oil, and PEG60 hardened castor oil); saturated or unsaturated monofatty acid glycerol ester having 8 to 18 carbon atoms such as caprylin (glycerol octanoate), glycerol monocaprate, glycerol monolaurate, glycerol monomyristate, glycerol monopalmitate, glycerol monostearate, and glycerol monooleate; difatty acid glycerol having 8 to 16 carbon atoms such as glycerol dioctanoate, glycerol dicaprate, glycerol dilaurate, glycerol dimyristate ester, and glycerol dipalmitate; α-tocopherol acetic acid ester, castor oil, soybean oil, cholesterol, squalene, squalane, lactose, ascorbylpalmitate, benzylbenzoate, methyl paraoxybenzoate, ethyl paraoxybenzoate, propyl paraoxybenzoate, butyl paraoxybenzoate, and the like. Incidentally, the "number of carbon atoms" in the stabilizer means the number of carbon atoms in the fatty acid component (acyl group) constituting the hydrophobic moiety.

The content of these other components is not particularly limited so long as it does not adversely affect the pH sensitive carrier and the natural immunity-activating substance, but the content is preferably 150 mol or less and more preferably more than 0 mol and 66.4 mol or less with respect to 100 mol of the amphipathic substance.

The adjuvant composition containing the pH sensitive carrier and the natural immunity-activating substance can effectively induce CTL by being administered together with an antigen.

That is, in the adjuvant composition, even when the natural immunity-activating substance is used in combination with the pH sensitive carrier, the function of the pH sensitive carrier, for example, the membrane disruptive function promoting effect (and the membrane fusion function promoting effect) can be suitably exhibited. In addition, when the natural immunity-activating substance is used together with the pH sensitive carrier, the function of the natural immunity-activating substance can also be suitably exhibited. The reason for this has not yet been elucidated, but the reason is inferred to be as follows.

That is, the pH sensitive carrier in its preferable form contains the pH sensitive compound and the amphipathic substance and has the membrane disruptive function promoting effect (in some cases, the membrane disruptive function promoting effect and the membrane fusion function promoting effect). At this time, the membrane disruptive function promoting effect (and the membrane fusion function promoting effect) is, as described above, based on a change in the association state of the pH sensitive carrier, caused by the pH sensitive compound in an acidic environment, and the rearrangement with the cell membrane, such as endosome, brought about by the amphipathic substance in this case. Herein, even when the natural immunity-activating substance is used in combination with the pH sensitive carrier, the pH sensitivity of the pH sensitive compound does not change, so that the pH sensitive compound can bring about a change in the association state of the pH sensitive carrier. In addition, whether the natural immunity-activating substance may, for example, be incorporated in the amphipathic substance or exist independently from the pH sensitive carrier, the rearrangement with the cell membrane by the amphipathic substance is not affected. Then, even when the natural immunity-activating substance is used in combination with the pH sensitive carrier, the function of the pH sensitive carrier is not impaired. In addition, the natural immunity-activating substance is, for example, only incorporated in the amphipathic substance of the pH sensitive carrier by the hydrophobic interaction or only exists independently from the pH sensitive carrier, so that its function is also not impaired. As a result, the adjuvant composition according to the present aspect, in a case where administered together with an antigen, can introduce the antigen into cytosol by the function of the pH sensitive carrier, and at the same time, can suitably induce cross-presentation based on the antigen introduced into the cytosol by the action of the natural immunity-activating substance, whereby CTL can be induced effectively.

Incidentally, the above-described reason is merely an inferred one, and any other effects produced by other causes will be included in the technical scope of the present invention.

Further, the adjuvant composition can also suitably induce humoral immunity.

As described above, an exogenous antigen is usually decomposed into peptide fragments by endosomes in antigen presenting cells and forms a complex with MHC class II molecules, to be presented to the CD4 positive T cells.

In a case where the adjuvant composition according to the present aspect induces CTL through cross-presentation of the antigen administered together with the adjuvant composition, the antigen and the natural immunity-activating substance may be introduced into cytosol when the pH sensitive carrier brings about rearrangement of the cell membrane of endosomes. However, in an embodiment, even if the rearrangement occurs, the antigen and the natural immunity-activating substance may partly or entirely remain in the endosomes. In addition, in an embodiment, in a case where the antigen and the adjuvant composition exist independently, taking-in of only the antigen may occur in part of the endosomes. Then, the antigen is decomposed into peptide fragments in the endosomes and forms a complex with MHC class II molecules, to be presented to CD4 positive T cells, whereby humoral immunity is induced. At this time, since the dendritic cells inducing the cross-presentation suitably are in an immunologically activated state, the induction of the humoral immunity is suitably developed. Alternatively, the dendritic cells inducing the cross-presentation suitably produce cytokine (for example, IFNγ) actively that activates immunity, thereby making the environment suitable for induction of immunity.

Therefore, the adjuvant composition can induce humoral immunity together with cross-presentation or in place of cross-presentation.

[Immune Checkpoint Inhibitor]

The adjuvant composition is used to be administered in combination with an immune checkpoint inhibitor.

Immune checkpoint receptors are present on T cells, and interact with ligands expressed on antigen presenting cells. T cells recognize an antigen presented onto the MHC molecule and are activated to generate an immune reaction, whereas the activation of T cells is controlled by an interaction between the immune checkpoint receptor and the ligand that occurs in parallel. The immune checkpoint receptors include co-stimulatory receptors and inhibitory receptors, and the T cell activation and the immune reaction are controlled by a balance between both receptors.

Cancer cells express a ligand for an inhibitory immune checkpoint receptor, and escape from attack of cytotoxic T cells utilizing the receptor.

The immune checkpoint inhibitor inhibits the action of the immune checkpoint of the receptor or ligand, and examples thereof include an antagonist against an inhibitory receptor and an agonist against a co-stimulatory immune checkpoint receptor.

The term "antagonist" includes various substances that interfere with receptor activation induced by binding between the receptor and the ligand. Examples thereof may include substances that interfere with the binding between the receptor and the ligand by binding to the receptor, and substances that interfere with the binding between the receptor and the ligand by binding to the ligand.

Examples of the antagonist against the inhibitory immune checkpoint include an antagonistic antibody that binds to an inhibitory immune checkpoint molecule (an inhibitory receptor or a ligand of the receptor), a soluble polypeptide that is designed based on an inhibitory immune checkpoint ligand and does not activate the receptor, or a vector capable of expressing the polypeptide, and the like.

Specific examples of the antagonist with respect to the inhibitory immune checkpoint receptor include an anti-PD-1 antibody, an anti-CTLA-4 antibody, an anti-LAG-3 antibody, an anti-TIM-3 antibody, an anti-BTLA antibody, and the like.

Examples of the antagonist against the ligand with respect to the inhibitory immune checkpoint receptor include an anti-PD-L1 antibody, an anti-PD-L2 antibody, an anti-CD80 antibody, an anti-CD86 antibody, an anti-GAL9 antibody, an anti-HVEM antibody, and the like.

Of them, from the viewpoint of obtaining a high antitumor effect by combination use with the adjuvant composition, the immune checkpoint inhibitor is preferably at least one selected from the group consisting of an anti-PD-1 antibody, an anti-PD-L1 antibody, an anti-PD-L2 antibody, and an anti-CTLA-4 antibody, more preferably an anti-PD-1 antibody and/or an anti-PD-L1 antibody, and further preferably an anti-PD-1 antibody.

Examples of the antibody such as an anti-PD-1 antibody, an anti-PD-L1 antibody, or an anti-PD-L2 include a monoclonal antibody, a polyclonal antibody, a single-stranded antibody, a modified antibody (for example, a "humanized antibody" in which only an antigen recognition part is humanized, or the like), a chimeric antibody, a bifunctional antibody capable of simultaneously recognizing two epitopes, a fragmented antibody (for example, F(ab')$_2$, Fab', Fab, or Fv fragments), and the like. The antibody may be any class of IgA, IgD, IgE, IgG, IgM, and the like. From the viewpoint of specific binding properties to the antigen, a monoclonal antibody is more preferably used.

The monoclonal antibody and the polyclonal antibody can be produced with reference to conventionally known methods.

As the antibody, a commercial product may be used.

<Method for Producing Adjuvant Composition>

As the method for producing the pH sensitive carrier, the method and the like described in WO 2013/180253 A (US 2013/323,320 A) can be appropriately referred to.

Specifically, as the method of associating the pH sensitive compound and the amphipathic substance, it is sufficient that the pH sensitive compound and the amphipathic substance are brought into contact with each other in an aqueous solution. Therefore, the pH sensitive carrier can be produced by bringing the pH sensitive compound and the amphipathic substance into contact with each other in an aqueous solution. Specifically, an aqueous solution containing the pH sensitive compound and the amphipathic substance is produced, and the solution is vigorously stirred for dispersion by using an emulsifier, a vortex mixer, ultrasonic waves, or the like, so that a pH sensitive carrier in which the pH sensitive compound and the amphipathic substance are associated can be obtained.

The method of preparing an aqueous solution containing a pH sensitive compound and an amphipathic substance is not particularly limited so long as the pH sensitive compound and the amphipathic substance form an associated product. Examples of the method include (1) a method in which an aqueous solution containing a pH sensitive compound and an aqueous solution containing an amphipathic substance are separately prepared, these aqueous solutions are mixed together, and the resulting solution is vigorously stirred for dispersion by using an emulsifier, a vortex mixer, ultrasonic waves, or the like to obtain a pH sensitive carrier; and (2) a preparation method using the Bangham method known as a method of preparing a liposome/micelle.

As the Bangham method, the following procedures are specifically exemplified.

First, in a glass container, constituent components of the pH sensitive carrier such as the pH sensitive compound and the amphipathic substance are dissolved in an organic solvent (for example, methanol or chloroform).

Specifically, it is preferable that a solution containing a pH sensitive compound having a pH sensitive compound dissolved in an organic solvent (for example, methanol or chloroform) and a solution containing a natural immunity-activating substance having an amphipathic substance dissolved in an organic solvent (for example, methanol or chloroform) are prepared, and the solution containing the pH sensitive compound and the solution containing the amphipathic substance are mixed. The mixing order at this time is not particularly limited, but the solution containing the pH sensitive carrier and the amphipathic substance may be mixed at one time or one of the solutions may be added to the other one thereof.

The concentration of the pH sensitive carrier in the solution containing the pH sensitive compound and the concentration of the amphipathic substance in the solution containing the amphipathic substance are not particularly limited and are appropriately set. The solution containing the amphipathic substance may contain an additive as necessary.

Then, the organic solvent of the mixed liquid is removed by a rotary evaporator or the like, causing a thin film to be formed on the wall of the glass container. Next, an aqueous solvent is added to the glass container in which the thin film has been formed, the thin film is thereby swelled at normal temperature (5 to 35° C.), and then, the glass container is shaken at normal temperature (5 to 35° C.). At this time, the thin film can be sufficiently dispersed in the aqueous solution by vigorous stirring with an emulsifier, a vortex mixer, or ultrasonic waves. Incidentally, as the aqueous solvent, the aqueous solvent contained in the adjuvant composition mentioned above can be used.

In this way, the dispersion (solution) of the pH sensitive carrier can be obtained. The dispersion of the pH sensitive carrier may be used without any changes in production of the adjuvant composition or the pH sensitive carrier may be separated from the dispersion.

Incidentally, as to the details of the Bangham method, reference can be made to known methods of producing liposomes as described in "Liposomes" (edited by Shoushichi Nojima, Jyunzou Sunamoto and Keizou Inoue, and published by Nankoudou) and "Liposomes in Life Science" (edited by Hiroshi Terada and Tetsuro Yoshimura, and published by Springer-Verlag, Tokyo).

Further, the adjuvant composition is not particularly limited and can be produced by various methods. Specifically, the method described in WO 2015/079952 A (US 2016/271, 246 A) and the like can be appropriately referred to.

For example, in the adjuvant composition in which the pH sensitive carrier and the natural immunity-activating substance independently exist, the adjuvant composition can be produced by mixing the pH sensitive carrier and the natural immunity-activating substance.

As the method of mixing the pH sensitive carrier and the natural immunity-activating substance, for example, a method in which a dispersion of the pH sensitive carrier obtained by the Bangham method and a solution containing the natural immunity-activating substance are mixed is exemplified. The mixing order at this time is not particularly limited, but the solution containing the pH sensitive carrier and the solution containing the natural immunity-activating substance may be mixed at one time or one of the solutions may be added to the other one thereof.

The solution containing the natural immunity-activating substance contains the natural immunity-activating substance and the aqueous solvent. Further, the solution may contain an additive as necessary. Incidentally, as the aqueous solvent, the aqueous solvent contained in the adjuvant composition mentioned above can be used.

Regarding the concentration of the natural immunity-activating substance in the solution containing the natural immunity-activating substance, the molar concentration of the natural immunity-activating substance is preferably 0.14 nmol/L to 0.227 mmol/L and more preferably 1.4 nmol/L to 0.19 mmol/L.

In the adjuvant composition in which the natural immunity-activating substance is supported on or embraced in the pH sensitive carrier, the adjuvant composition can be produced by associating the pH sensitive carrier and the natural immunity-activating substance.

As the method of associating the pH sensitive compound, the amphipathic substance, and the natural immunity-activating substance, it is sufficient that the pH sensitive compound, the amphipathic substance, and the natural immunity-activating substance are brought into contact with each other in an aqueous solution.

The method of bringing the pH sensitive compound, the amphipathic substance, and the natural immunity-activating substance into contact with each other in an aqueous solution is not particularly limited so long as they form an associated product. Examples of the method include (1) a method in which an aqueous solution containing the pH sensitive compound, and an aqueous solution containing the amphipathic substance, and an aqueous solution containing the natural immunity-activating substance are separately prepared, these aqueous solutions are mixed together, and the resulting solution is vigorously stirred for dispersion by using an emulsifier, a vortex mixer, ultrasonic waves, or the like to obtain an adjuvant composition; (2) a preparation method using the Bangham method known as a method of preparing a liposome; and the like. Specific procedures of the Bangham method are the same as described in the section of the method for producing the pH sensitive carrier.

Incidentally, the method of adding other components such as a stabilizer which may be contained in the adjuvant composition containing the aqueous solvent as a component is not particularly limited. For example, other components may be added to the aqueous solution containing the pH sensitive compound, the aqueous solution containing the amphipathic substance, and/or the aqueous solution containing the natural immunity-activating substance, or when a thin film is prepared by the Bangham method, other components may be dissolved together with the pH sensitive carrier or the constituent components of the adjuvant composition and the aqueous solution containing the adjuvant composition may be obtained using the thin film containing those components.

<Vaccine Composition>

The vaccine composition contains an adjuvant composition and an antigen.

[Adjuvant Composition]

As the adjuvant composition, the same one as aforementioned can be used, and, hence, description thereof is omitted here.

[Antigen]

The antigen is not particularly limited so long as it produces immune response, and is preferably a peptide or a protein.

Examples of the peptide or protein include virus antigen, bacterial antigen, mycotic antigen, protozoan or verminous antigen, cancer antigen, and the like.

The virus antigen is not particularly limited, and examples thereof include human immunodeficiency virus (HIV) antigen such as gene product of gag, pol, and env genes, Nef protein, reverse transcriptase, and other HIV components; hepatitis virus antigen such as S, M, and L proteins of hepatitis B virus, pre-S antigen of hepatitis B virus, hepatitis C virus RNA, and virus components of hepatitis A, B, and C; influenza virus antigen such as hemagglutinin, neuraminidase, and other influenza virus components; measles virus antigen; rubella virus antigen; rotavirus antigen; cytomegalovirus antigen; respiratory syncytial virus antigen; herpes simplex virus antigen; varicella zoster virus antigen; Japanese encephalitis virus antigen; and rabies virus antigen. Other examples thereof include peptides derived from adenovirus, retrovirus, picornavirus, herpesvirus, rotavirus, hantavirus, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongy virus.

The bacterial antigen is not particularly limited, and examples thereof include bacterial antigen such as pertussis toxin, filamentous hemagglutinin, pertactin, FIM2, FIM3, cyclase adenylate, and other pertussis bacterial antigen components; diphtheria bacterial antigen such as diphtheria toxin or toxoid, and other diphtheria bacterial antigen components; bacterial antigen of tetanus *bacillus* and *streptococcus* such as tetanus toxin or toxoid, and other tetanus bacterial antigen components; Gram-negative bacillary bacterial antigen such as lipopolysaccharide, and other Gram-negative bacterial antigen components; tubercle *bacillus* bacterial antigen such as mycolic acid and mycobacteria antigen components; *helicobacter* and *pylori* bacterial antigen components; *pneumococcus* bacterial antigen; influenza *bacillus* bacterial antigen; anthrax *bacillus* bacterial antigen; *rickettsia* bacterial antigen; and the like.

The mycotic antigen is not particularly limited, and examples thereof include *candida* mycotic antigen components; *histoplasma* mycotic antigen; *cryptococcus* mycotic antigen; *coccidioides* mycotic antigen; ringworm mycotic antigen; and the like.

The protozoan or verminous antigen is not particularly limited, and examples thereof include *Plasmodium falciparum* antigen; *toxoplasma* antigen; *schistosoma* antigen; *Leishmania* antigen; trypanosome *cruzi* antigen; and the like.

The cancer antigen is not particularly limited, and examples thereof include those cancer antigens derived from the cell surface of cells of tumor tissue, protoplasm, nuclei, cell organelles, and the like. Examples of the cancer include leukemia, lymphoma, nervous tumor, melanoma, breast cancer, lung cancer, head and neck cancer, stomach cancer, colon cancer, liver cancer, pancreatic cancer, cancer of the uterine cervix, uterine cancer, ovarian cancer, vaginal cancer, testis cancer, prostatic cancer, penile cancer, bone tumors, hemangioma, lip cancer, cancer of epipharynx, pharyngeal cancer, carcinoma of esophagus, rectal cancer, carcinoma of the gallbladder, cancer of the bile duct, laryngeal cancer, bladder carcinoma, kidney cancer, brain tumor, thyroid carcinoma, Hodgkin's disease, non-Hodgkin lymphoma, and the like. Incidentally, specific examples of the cancer antigen include HER2/neu (Human EGFR related 2), CEA (Carcinogenic Embryonic Antigen), MAGE (Melanoma-associated Antigen), XAGE (X antigen family member), NY-ESO-1, gp100, Melan/mart-1, Tyrosinase, PSA (Prostate Specific Antigen), PAP (Prostate Acid Phosphatase), K-ras, N-ras, Bcr-Abl, MUC-1 (Mucin-1), PSMA (Prostate Specific Membrane Antigen), survivin, WT-1 (Wilmstumor suppressor gene 1), AFP (AlphaFetoprotein), GPC (Glypican), EGFR (Epidermal Growth Factor Receptor), and the like.

The aforementioned antigens may be used singly or in combination of two or more kinds thereof.

The content of the antigen is preferably 3.2 μg to 1.0 mg with respect to 100 nmol of the amphipathic substance constituting the pH sensitive carrier.

A rate in which the antigen is to be incorporated is not particularly limited; while the antigen and the adjuvant composition may exist independently, the incorporation rate is preferably 3% or more, more preferably 5 to 80%, and more preferably 10 to 60%. When the incorporation rate is 3% or more, for example, when endocytosis of the vaccine composition into cells occurs, the antigen is highly possibly introduced into the endosome into which the adjuvant composition is introduced, and the effect of the invention can be suitably obtained, which is preferable. Incidentally, the term "incorporation rate of the antigen" means mainly the portion in which the antigen is supported on or embraced in the adjuvant composition, and, as the value of the incorporation rate, the values measured by the method described in [0195] to [0198] of WO 2015/079952 A ([0312] to [0315] of US 2016/271,246 A) are to be adopted.

[Additives]

The vaccine composition may contain other pharmaceutical additives.

The usable additives vary depending on the dosage form of the vaccine composition. At this time, the vaccine composition may be a solid preparation such as tablet, powder, and capsule or may be a liquid preparation such as an injection preparation, but is preferably a liquid preparation. Incidentally, in the case of a liquid preparation, the vaccine composition may be provided as a dried product which is regenerated with water or other suitable excipient at the time of use.

In a case where the vaccine composition is a liquid preparation, the vaccine composition may contain a solvent (such as a physiological saline solution, sterilized water, or a buffer solution), a membrane stabilizer (such as cholesterol), a tonicity agent (such as sodium chloride, glucose, or glycerin), an antioxidant (such as tocopherol, ascorbic acid, or glutathione), a preservative (such as chlorbutanol or paraben), and the like. Incidentally, the solvent may be a solvent used in production of the vaccine composition.

According to an embodiment of the present invention, the vaccine composition can efficiently induce cell-mediated immunity by the cross-presentation of the antigen. According to this, for example, a lot of CTLs can be induced. Incidentally, in the present specification, the expression "to induce CTL" means that formation of many spots can be obtained in the ELispot method described in the present specification as compared to a control, which is not treated with the vaccine composition (that is, a mixture of the antigen and the natural immunity-activating substance).

Further, according to another embodiment of the present invention, the vaccine composition can induce humoral immunity. According to this, an antibody such as IgG can be produced. At this time, the expression "to induce humoral immunity" means that a high IgG antibody titer is obtained as compared to a control to which the antigen is administered.

The vaccine composition of the present aspect, when administered to a subject and with the external environment thereof decreasing in pH less than the physiological pH (for example, pH 6.5), develops the membrane disruptive function promoting effect or the membrane disruptive function promoting effect and the membrane fusion function promoting effect, thus enabling an antigen to be efficiently released to cytosol. Then, cell-mediated immunity and CTL can be suitably induced, and immunity can be imparted.

<Method for Producing Vaccine Composition>

The vaccine composition according to the present embodiment is not particularly limited and can be produced by various methods. Specific examples of the method for producing the vaccine composition include a preparation method by dispersion, a preparation method by mixing, a preparation method by freeze-thawing and freeze-drying, and the like. Specifically, the method described in WO 2015/079952 A (US 2016/271,246 A) and the like can be appropriately referred to.

(Preparation Method by Dispersion)

The preparation method by dispersion includes a step of mixing the pH sensitive compound, the amphipathic substance, the natural immunity-activating substance, and the antigen. Specifically, on a wall of a glass container, a thin film containing constituent components of the adjuvant composition is formed. Then, a solution containing the antigen is added to the glass container in which the thin film is formed, the thin film is swelled at 5 to 35° C., and then the glass container is shaken. At this time, a vaccine composition is prepared by a method of vigorously stirring the solution for dispersion by using an emulsifier, a vortex mixer, or ultrasonic waves. Alternatively, on a wall of a glass container, a thin film containing the pH sensitive compound and the amphipathic substance is formed, a solution containing the antigen and the natural immunity-activating substance is then added to the glass container in which the thin film is formed, the thin film is swelled at 5 to 35° C., and then the glass container is shaken. At this time, a vaccine composition is prepared by a method of vigorously stirring the solution by using an emulsifier, a vortex mixer, or ultrasonic waves.

The solution containing the antigen and the solution containing the antigen and the natural immunity-activating substance may be the same ones or the referenced ones as prepared by a preparation method by mixing described later.

(Preparation Method by Mixing)

The preparation method by mixing includes a step of mixing a solution of the pH sensitive compound, a solution containing the amphipathic substance, a solution containing the natural immunity-activating substance, and a solution containing the antigen.

Specifically, the pH sensitive carrier and the natural immunity-activating substance are mixed to obtain an adjuvant composition, and the dispersion of the adjuvant composition and the antigen or the solution containing the antigen are then mixed, so that a vaccine composition can be obtained.

The solution containing the antigen preferably contains the antigen and the aqueous solvent. Further, the solution may contain an additive as necessary. Incidentally, as the aqueous solvent, the aqueous solvent contained in the adjuvant composition mentioned above can be used.

The concentration of the antigen in the solution containing the antigen is appropriately set according to the type of antigen, but the molar concentration of the antigen is, for example, 32 mg/L to 10 g/L.

The method of mixing the dispersion of the adjuvant composition mentioned above and the solution containing the antigen is not particularly limited. The obtained mixed liquid is preferably dispersed, and the dispersing can be performed, for example, by using an emulsifier, a vortex mixer, ultrasonic waves, and the like.

(Preparation Method by Freeze-Thawing and Freeze-Drying)

The preparation method by freeze-thawing and freeze-drying includes a step of freeze-thawing the solution obtained by the preparation method by dispersion or the preparation method by mixing to prepare a molten solution and a step of freeze-drying the molten solution.

Step of Preparing Molten Solution

The molten solution can be prepared by freeze-thawing the solution obtained by the preparation method by dispersion or the preparation method by mixing.

The freeze-thawing means that the solution is freeze-dried and then the obtained dried product is melted.

The method for freeze-drying is not particularly limited, but a method of subliming water using liquefied nitrogen, cooled methanol, or the like is preferred.

Further, the method for melting the dried product is not particularly limited, but a method of heating the dried product obtained by cooling or a method of adding a solvent is preferred.

Step of Freeze-Drying

This step is a step of freeze-drying the molten solution obtained above.

The method for freeze-drying is not particularly limited similarly to the above-described case, but a method of subliming water using liquefied nitrogen, cooled methanol, or the like is preferred.

<Combination Use of Adjuvant Composition and Immune Checkpoint Inhibitor>

The adjuvant composition and the immune checkpoint inhibitor are used in combination.

Therefore, the adjuvant composition containing the pH sensitive carrier and the natural immunity-activating substance is used to be administered in combination with an immune checkpoint inhibitor.

The administration order of the adjuvant composition and the immune checkpoint inhibitor is not particularly limited, and the adjuvant composition and the immune checkpoint inhibitor may be administered simultaneously or in a staggered manner. Further, in the case of administration in a staggered manner, the immune checkpoint inhibitor may be administered after the adjuvant composition is administered or the adjuvant composition may be administered after the immune checkpoint inhibitor is administered.

The immune checkpoint inhibitor acts on the immune checkpoint receptor-ligand on T cells to obtain the effect. When the immune checkpoint inhibitor is administered after the T cells are induced, since enhancement in antitumor effect is considered to be developed, it is preferable that the immune checkpoint inhibitor is administered after the adjuvant composition containing the pH sensitive carrier and the natural immunity-activating substance is administered. Therefore, it is preferable that the adjuvant composition is administered before the immune checkpoint inhibitor is administered. Incidentally, in the administration aspect in a staggered manner, administration routes may be the same as or different from each other so long as administration is performed in a staggered manner.

Furthermore, a preferred aspect of the present embodiment is a vaccine composition being used to be administered in combination with an immune checkpoint inhibitor, the vaccine composition containing an adjuvant composition, which contains a pH sensitive carrier and a natural immunity-activating substance, and an antigen.

The administration order of the vaccine composition and the immune checkpoint inhibitor is not particularly limited, and the vaccine composition and the immune checkpoint inhibitor may be administered simultaneously or in a staggered manner. Further, in the case of administration in a staggered manner, the immune checkpoint inhibitor may be administered after the vaccine composition is administered or the vaccine composition may be administered after the immune checkpoint inhibitor is administered.

From the viewpoint of further exhibiting enhancement in antitumor effect, it is preferable that the immune checkpoint inhibitor is administered after the vaccine composition is administered. Therefore, it is preferable that the vaccine composition is administered before the immune checkpoint inhibitor is administered. Incidentally, in the administration aspect in a staggered manner, administration routes may be the same as or different from each other so long as administration is performed in a staggered manner.

As preparation of the adjuvant composition and the immune checkpoint inhibitor, a composition (single preparation) containing the adjuvant composition and the immune checkpoint inhibitor, a combination (drug kit) of independently preparing the adjuvant composition and the immune checkpoint inhibitor and then combining those components, and the like are exemplified. In a preferred aspect, the adjuvant composition and the immune checkpoint inhibitor are independently prepared and then combined. That is, in the present aspect, a drug kit in which the adjuvant composition, which contains the pH sensitive carrier and the natural immunity-activating substance, and the immune checkpoint inhibitor are combined is preferred. The details of the pH sensitive carrier, the natural immunity-activating substance, the immune checkpoint inhibitor are as described above. Further, in the drug kit, the administration order of the adjuvant composition and the immune checkpoint inhibitor is not particularly limited, and the adjuvant composition and the immune checkpoint inhibitor may be administered simultaneously or in a staggered manner. Further, in the case of administration in a staggered manner, the immune checkpoint inhibitor may be administered after the adjuvant composition is administered or the adjuvant composition may be administered after the immune checkpoint inhibitor is administered. From the viewpoint of further exhibiting enhancement in antitumor effect, it is preferable that the adjuvant composition is administered and then the immune checkpoint inhibitor is administered. According to such an aspect, a significant antitumor effect can be obtained. Incidentally, in the administration aspect in a staggered manner, administration routes may be the same as or different from each other so long as administration is performed in a staggered manner.

Furthermore, a preferred aspect of the present embodiment is a drug kit in which a vaccine composition, which contains an adjuvant composition containing a pH sensitive carrier and a natural immunity-activating substance and an antigen, and an immune checkpoint inhibitor are combined. A still another aspect is a drug kit in which an adjuvant composition, which contains a pH sensitive carrier and a natural immunity-activating substance, an antigen, and an immune checkpoint inhibitor are combined. According to the drug kit of the present invention, a high antitumor effect can be obtained. In the drug kit, the administration order of the vaccine composition or the adjuvant composition and the antigen, and the immune checkpoint inhibitor is not particularly limited, and administration may be performed simultaneously or in a staggered manner. Further, in the case of administration in a staggered manner, the immune checkpoint inhibitor may be administered after the vaccine composition or the adjuvant composition and the antigen are administered or the vaccine composition or the adjuvant composition and the antigen may be administered after the immune checkpoint inhibitor is administered. From the viewpoint of further exhibiting enhancement in antitumor effect, it is preferable that the vaccine composition or the adjuvant composition and the antigen are administered and then the immune checkpoint inhibitor is administered.

Further, the drug kit is preferably a drug kit for the treatment or prevention of cancer. Specific examples of the cancer include leukemia, lymphoma, nervous tumor, melanoma, breast cancer, lung cancer, head and neck cancer, stomach cancer, colon cancer, liver cancer, pancreatic cancer, cancer of the uterine cervix, uterine cancer, ovarian cancer, vaginal cancer, testis cancer, prostatic cancer, penile cancer, bone tumors, hemangioma, lip cancer, cancer of epipharynx, pharyngeal cancer, carcinoma of esophagus, rectal cancer, carcinoma of the gallbladder, cancer of the bile duct, laryngeal cancer, bladder carcinoma, kidney cancer, brain tumor, thyroid carcinoma, Hodgkin's disease, non-Hodgkin lymphoma, and the like.

The administration aspect in the case of administering the adjuvant composition and the immune checkpoint inhibitor in combination is not particularly limited so long as administration routes, administration frequencies, and dosage amounts that are respectively suitable are employed, and examples thereof include (1) administration of a composition containing the adjuvant composition and the immune checkpoint inhibitor, that is, administration as single preparation, (2) simultaneous administration in the same administration route of two types of preparations obtained by individually preparing the adjuvant composition and the immune checkpoint inhibitor, (3) administration in a staggered manner in the same administration route of two types of preparations obtained by individually preparing the adjuvant composition and the immune checkpoint inhibitor, (4) simultaneous administration in different administration routes of two types of preparations obtained by individually preparing the adjuvant composition and the immune checkpoint inhibitor, (5) administration in a staggered manner in different administration routes of two types of preparations obtained by individually preparing the adjuvant composition and the immune checkpoint inhibitor, and the like.

As a preferable administration aspect in combination use administration, there is mentioned a method in which the adjuvant composition or the vaccine composition is administered and then the immune checkpoint inhibitor is administered.

Another aspect of the present invention is a method for treating or preventing a disease including administering an effective amount of an adjuvant composition containing a pH sensitive carrier and a natural immunity-activating substance and an effective amount of an immune checkpoint inhibitor to a subject requiring treatment or prevention. Further, another aspect of the present invention is a method for treating or preventing a disease including administering an effective amount of a vaccine composition containing an adjuvant composition, which contains a pH sensitive carrier and a natural immunity-activating substance, and an antigen, and an effective amount of an immune checkpoint inhibitor to a subject requiring treatment or prevention. In particular, the disease is preferably a cancer.

The above-described subject is preferably a mammal, particularly preferably a human.

Further, in a case where the adjuvant composition or the vaccine composition and the immune checkpoint inhibitor are administered in a staggered manner, it is necessary to administer the immune checkpoint inhibitor with a time interval sufficient for enhancement in antitumor effect. A specific time interval for administration is appropriately determined depending on an individual case in consideration of the symptom, age, gender, or the like of a patient.

Further, it is preferable to administer the vaccine composition and the immune checkpoint inhibitor in a certain cycle. As an administration cycle, it is preferable to appropriately adjust the administration cycle so as to be suitable for combination use. Specific administration frequencies, dosage amounts, time of infusion administration, administration cycles, and the like are appropriately determined depending on an individual case in consideration of the symptom, age, gender, or the like of a patient.

The single administration of the immune checkpoint inhibitor is conventionally known, and for example, the immune checkpoint inhibitor is administered multiple times from once per day in a range of 2 to 3 mg/kg/Day.

In the case of using the adjuvant composition and the immune checkpoint inhibitor in combination, by an administration route for typical administration, the dosage amount thereof can be set to the same dosage amount as in the case of typical single administration or set to be an amount lower than the dosage amount in the case of single administration (for example, 0.10 to 0.99 times the maximum dosage amount in the case of single administration).

The dosage amount of the adjuvant composition is appropriately determined depending on an individual case in consideration of the symptom, age, gender, or the like of a patient.

Further, the mass (mg/kg/Day) ratio of the dosage amount of the immune checkpoint inhibitor and the adjuvant composition is also appropriately determined depending on an individual case in consideration of the symptom, age, gender, or the like of a patient.

The methods for administering the adjuvant composition, the vaccine composition, and the immune checkpoint inhibitor are not particularly limited, and examples thereof include oral administration; parenteral administration such as intravenous injection, intraarterial injection, subcutaneous injection, intracutaneous injection, intraperitoneal administration, intramuscular injection, intraspinal injection, percutaneous administration, or percutaneous absorption; and the like. For example, in the case of using a peptide and a protein as antigens, preferred is administration through a parenteral route, particularly, administration by subcutaneous injection, intracutaneous injection, intramuscular injection, or intravenous injection. Incidentally, a vaccine composition in which the antigen is independently mixed without being supported on or embraced in the adjuvant composition is preferably administered in the form of local administration, specifically, subcutaneous administration, intracutaneous administration, or intramuscular administration. Further, the immune checkpoint inhibitor is preferably administered in the form of intraperitoneal administration.

EXAMPLES

The advantageous effects of the present invention will be described below by way of Examples and Comparative Examples. The expression "part (s)" or "%" may be used in the following Examples, and it indicates "part (s) by weight" or "% by weight." Further, unless specified otherwise, each operation is carried out at room temperature (25° C.).

1. Reagent

Sodium deoxycholate (pharma-grade, purchased from Sigma-Aldrich Co., LLC.)

DLPC (1,2-dilauroyl-sn-glycero-3-phosphatidylcholine: purchased from NOF CORPORATION, COATSOME MC-1212)

EYPC (non-hydrogenated egg yolk phosphatidylcholine: made by NOF CORPORATION, COATSOME NC-50)

Oligonucleotide comprising a CpG motif (CpG-ODN: purchased from InvivoGen, ODN-2395, SEQ NO.; 5'-tcgtcgtttt cggcgcgcgccg-3' (SEQ NO. 1) (in the sequence, the underlined part represents palindrome sequence)

PBS (purchased from NACALAI TESQUE, INC., phosphate buffered saline (not containing KCl) (pH 7.4))

MES-Na (purchased from Merck KGaA, Darmstadt, Germany)

Sodium chloride (purchased from KANTO CHEMICAL CO., INC.)

PBS Tablets (Phosphate buffered saline: purchased from Takara Bio Inc.)

Sodium hydroxide aqueous solution (0.1 mol/L: purchased from NACALAI TESQUE, INC.)

Hydrochloric acid (0.1 mol/L, 1 mol/L: purchased from NACALAI TESQUE, INC.)

Phospholipid C-test Wako (purchased from Wako Pure Chemical Industries, Ltd.)

Pyranine (purchased from Tokyo Chemical Industry Co., Ltd.)

DPX (p-xylene-bis-pyridinium bromide: purchased from Molecular Probes, Inc.)

Triton-X100 (purchased from Wako Pure Chemical Industries, Ltd.)

Anti-PD-1 antibody (purchased from eBioscience, anti-mouse PD-1 (CD279) FG Purified RMP1-14 (Bio X Cell))

Methanol (purchased from NACALAI TESQUE, INC.)

Chloroform (purchased from Wako Pure Chemical Industries, Ltd.)

OVA protein (OVAlbumin: purchased from Wako Pure Chemical Industries, Ltd., ovalbumin low endotoxin) (hereinafter, also simply referred to as "OVA")

OVA peptide: SIINFEKL (outsourced for synthesis by PH Japan Co., Ltd.) (hereinafter, also simply referred to as "peptide")

RPMI (purchased from NACALAI TESQUE, INC., RPMI 1640 culture medium (liquid))

Penicillin-Streptamycin Mixed Solution (purchased from NACALAI TESQUE, INC.)

FBS (Fetal Bovine Serum, Certified, Heat Inactivatied, US Origin: purchased from Gibco)

RBC lysis buffer (purchased from Santa Cruz Biotechnology, Inc.): erythrocyte hemolytic buffer Mouse IFNγ ELISPOT Set (purchased from BD Biosciences, Inc.)

AEC Substrate Set (purchased from BD Biosciences, Inc.)

"Animals"

C57BL/6N mice, female, (6 weeks old), were bought from Japan S.L.C, Inc. Experiments were carried out according to the guideline for animal experiments drafted by Terumo Corporation.

"Cells"

Regarding E-G7-OVA cells (ATCC No. CRL-2113, hereinafter, also simply described as EG7 cells), cells purchased from ATCC were cultured and used.

"Cell Culture"

Cell culture was carried out using an incubator (MCO20AIC) set to 5% $CO_2$ and 37° C.

"Sample Preparation, Etc."

RPMI Medium

Penicillin (100 unit/mL) and streptomycin (100 mg/mL) were added as antibiotics. Further, FBS was additionally added, as necessary, to obtain a 10% serum-containing RPMI medium.

2. Preparation of Administration Liquid (Preparation of pH Sensitive Carrier)

1000 nmol of DLPC, which is an amphipathic substance, dissolved in chloroform and 1600 nmol of sodium deoxycholate, which is a pH sensitive compound, dissolved in methanol were mixed in a 10 mL eggplant flask and the solvent was volatilized by a rotary evaporator to produce a thin film. To the produced thin film, 0.5 mL of PBS was added and dispersed using an ultrasonic irradiator (USC-J, manufactured by Iuchi Seieido Co., Ltd.) to prepare a dispersion (solution) of the pH sensitive carrier (concentrations of DLPC and sodium deoxycholate: 5.2 mmol/L).

(Production of Temporary Solution of Oligonucleotide Comprising CpG Motif)

The oligonucleotide comprising a CpG motif was dissolved using sterilized water (endotoxin-free) that is an accompanying solubilization liquid to be 1 μg/μL, thereby obtaining a temporary solution.

(Preparation of Adjuvant Composition)

A temporary solution of a natural immunity-activating substance was added to the dispersion (solution) of the pH sensitive carrier prepared above and then mixed. Additional PBS was added thereto in order to adjust the concentration of the mixture and then mixed to prepare an adjuvant composition.

(Temporary Solution of OVA)

2 mg of OVA (model antigen) was dissolved in 1.0 mL of PBS to obtain a temporary solution of OVA.

(Administration Liquid of Anti-PD-1 Antibody)

Regarding the administration liquid of the anti-PD-1 antibody, a purchased antibody stock solution was diluted with PBS 10-fold to obtain an administration liquid (anti-PD-1 antibody 0.1 g/L).

3. Leaching Test: Measurement of Leakage

The leakage was determined according to the method described by K. Kono et al. Bioconjugate Chem. 2008191040-1048 and evaluated using an EYPC liposome including Pyranine serving as a fluorescent substance and DPX serving as a quencher.

3000 nmol of EYPC dissolved in chloroform was measured and placed in a 10 mL eggplant flask and converted to a thin film by using a rotary evaporator. 500 μL of a Pyranine solution (Pyranine: 35 mM, DPX: 50 mM, MES-Na: 25 mM, pH 7.4) was added, followed by dispersion using an ultrasonic irradiator (USC-J) and passage through a polycarbonate film having a pore size of 100 nm using an extruder to obtain a uniform particle size. Using an MES Buffer and a G100 column, an outer water layer was substituted to obtain a dispersion of EYPC liposomes including the fluorescent substance. The concentration of the phospholipid was determined using phospholipid C-test Wako and was adjusted using an MES Buffer such that phospholipid would be 1.0 mmol/L.

20 μL of the EYPC liposome dispersion whose concentration had been adjusted, and 20 μL of an evaluation sample dispersion were charged into 2960 μL of the MES Buffer whose pH had been adjusted, and after incubation at 37° C. for 90 or 30 minutes (in Examples, unless otherwise stated, the results of 90 minutes were shown), fluorescences at Ex 416 and Em 512 nm were observed using a spectrophotometer FP-6500 to monitor the Leakage.

Incidentally, the leakage was calculated in such a way that in a case where the dispersion alone of EYPC liposomes was used, it was taken as 0% and a value obtained in a case where 30 μL of a 10-fold diluted Triton-X100 was added was taken as 100%. Specifically, the leakage was calculated according to the following formula. Incidentally, in the following formula, a measured fluorescence intensity is denoted by L, a fluorescence intensity of a dispersion alone of EYPC liposomes including a fluorescent substance is denoted by $L_0$, and a fluorescent substance in a case where Triton-X100 was added is denoted by $L_{100}$.

$$\text{Leakage}(\%) = \frac{(L - L_0)}{(L_{100} - L_0)} \times 100 \qquad [\text{Math. 3}]$$

Regarding the adjuvant composition adjusted above, the leakages of the pH sensitive carrier, the pH sensitive compound, and the amphipathic substance at a pH of 7.4 and a pH of 5.0 were measured and Δ and Δ' were calculated by the following formulas.

[Math. 4]

$$\Delta = (Lc_x - Lc_{7.4}) - (La_x - La_{7.4}) > 0 \qquad \text{Formula (1)}$$

$$\Delta' = Lc_x - (La_x + Lb_x) > 0 \qquad \text{Formula (2)}$$

As a result, Δ was 40.9 and Δ' was 39.8. Thus, the adjuvant composition has a membrane disruptive function promoting effect.

[Evaluation Method 1: Confirmation of CTL Induction Using ELIspot Method]

The induction of CTL was confirmed using the ELIspot method. Test substances are a mixture of OVA and CpG-ODN (OVA+CpG-ODN), a mixture (vaccine composition) of OVA, CpG-ODN, and the pH sensitive carrier (OVA+CpG-ODN+the pH sensitive carrier), and a mixture of OVA and the pH sensitive carrier (OVA+the pH sensitive carrier).

Incidentally, samples used for administration were prepared using an administration liquid prepared according to "Preparation of Administration Liquid." Further, the mixture of OVA, CpG-ODN, and the pH sensitive carrier was obtained by adding a temporary solution of OVA to the adjuvant composition and mixing the resultant product by ultrasonic waves.

(1) Immunization of Mice Administration was performed under anesthesia. Administration was carried out by subcutaneous injection, 100 μL/head, at one position on the back. The pH sensitive carrier was set as follows: the amphipathic substance: 10 nmol/head and the pH sensitive compound: 16 nmol/head. The natural immunity-activating substance, in the case of CpG-ODN, was set to 10 μg (1.42 nmol)/head. As the antigen, OVA was used as a model antigen and set to 80 μg/head. The administration was performed once, and assay was performed 7 days after the administration (n=1).

(2) ELispot Method

The mice were sacrificed on the seventh day after the last administration in the immunization to the mice and its spleen was extracted. After addition of 3.0 mL of 10% serum-containing RPMI medium, the spleen was treated by the BD Falcon cell strainer to obtain a suspension of cells. The cells were subjected to hemolysis using an RBC lysis buffer, and then the cells were washed using the 10% serum-containing RPMI medium. The cells were dispersed in the 10% serum-containing RPMI medium, the number of cells was then counted, and a dispersion of spleen cells was obtained.

The ELIspot method was carried out by using the Mouse IFNγ ELISPOT Set. On day before inoculation of the dispersion of spleen cells, the 96-well ELIspot plate was allowed to adsorb the detection antibody attached to the drug kit, to produce a plate. The produced plate was washed with 10% serum-containing RPMI medium, 200 μL of 10% serum-containing RPMI medium was then added thereto, and the plate was left to stand at 37° C. for 2 hours for blocking. The plate was washed with 10% serum-containing RPMI medium, and 100 μL of 10% serum-containing RPMI medium containing 40 μg/mL of OVA peptide was then added to the plate. The plate was inoculated with the dispersion of spleen cells so as to be 2×10' cells/well, and finally, 10% serum-containing RPMI medium was used so that the total amount per well was adjusted to 200 μL. Thereafter, cultivation was performed for two nights, and coloration of the plate was conducted.

The coloration of the plate was carried out according to the protocol described in the Mouse IFNγ ELISPOT Set and the AEC Substrate Set.

Figure 3C:
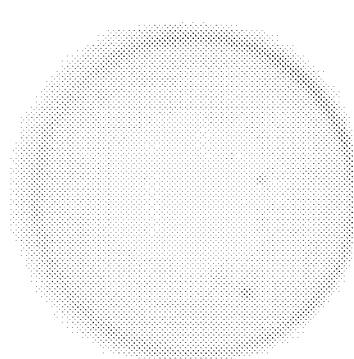

The obtained results are shown in FIGS. 3(A)-3(C).

The mixture of OVA and CpG-ODN (FIG. 3(A)) formed few spots and only a small number of CTLs could be induced.

On the other hand, the mixture of OVA, CpG-ODN, and the pH sensitive carrier (FIG. 3(B)) formed many spots and a large number of CTLs could be induced. Thus, it is shown that the adjuvant composition being contained leads to induction of a large number of CTLs. It is considered that as a result that the pH sensitive carrier induces the antigen presentation by a number of MHC class I molecules to the matured antigen presenting cell, a number of CTLs are induced.

Further, the mixture of OVA and the pH sensitive carrier (FIG. 3(C)) not using CpG-ODN that is a natural immunity-activating substance could not form a spot and CTL was not induced. The reason for this is considered that even if the natural immunity-activating substance is not contained, the number of matured antigen presenting cells did not increase, so that CTL could not be induced.

[Evaluation Method 2: Confirmation of Antitumor Effect Using Mouse Tumor-Bearing Experimental System]

Subsequently, the antitumor effect was confirmed using the mouse tumor-bearing experimental system. Mice were divided into seven groups: Group 1: without treatment, Group 2: administration of OVA, Group 3: administration of OVA and the anti-PD-1 antibody, Group 4: administration of OVA and CpG-ODN, Group 5: administration of OVA, CpG-ODN, and the pH sensitive carrier (in the drawing, described as micelle), Group 6: administration of OVA and CpG-ODN, and the anti-PD-1 antibody, and Group 7: administration of OVA, CpG-ODN and the pH sensitive carrier, and the anti-PD-1 antibody. The sample used in administration was prepared using the administration liquid prepared according to "Preparation of Administration Liquid." Further, as the mixture of OVA, CpG-ODN, and the pH sensitive carrier, the vaccine composition obtained by adding the temporary solution of OVA to the adjuvant composition and mixing the resultant product with ultrasonic waves was used.

(1) Construction of Evaluation System and Immunization of Mice

All of administrations were performed under anesthesia. On Day 0, EG7 cells were injected subcutaneously to mice at 5×10$^5$ cells/head and then cancer-bearing was conducted. Administration liquids containing comparative samples (only OVA (Group 2 and Group 3), OVA and CpG-ODN (Group 4 and Group 6)), and a vaccine composition (a mixture of OVA, CpG-ODN, and the pH sensitive carrier) (Group 5 and Group 7) were injected subcutaneously at 20 μL/shot, and administration was performed three times on the schedule of Day 5, Day 12, and Day 19. Administration of the anti-PD-1 antibody (Group 3, Group 6, and Group 7) was performed in such a manner that an administration liquid of the anti-PD-1 antibody was injected intraperitoneally at 500 μL/shot and administration was performed three times on the schedule of Day 8, Day 15, and Day 22. Since an individual difference was large, one group was configured by five mice. The pH sensitive carrier per administration was set as follows: the amphipathic substance: 2 nmol/head and the pH sensitive compound: 3.2 nmol/head. The natural immunity-activating substance, in the case of CpG-ODN, was set to 2 μg (0.284 nmol)/head. Regarding the antigen, OVA was used as a model antigen and set to 16 μg/head.

(2) Measurement of Tumor Size

Regarding the size of the tumor (cancer), the major axis a and the minor axis b of the tumor were measured using a digital caliper and a volume was obtained using the calculation formula of Formula 1). Individuals reaching the end point underwent euthanasia.

[Math. 5]

$$V = 0.5ab^2 \qquad \text{Formula 1)}$$

Figure 4A:
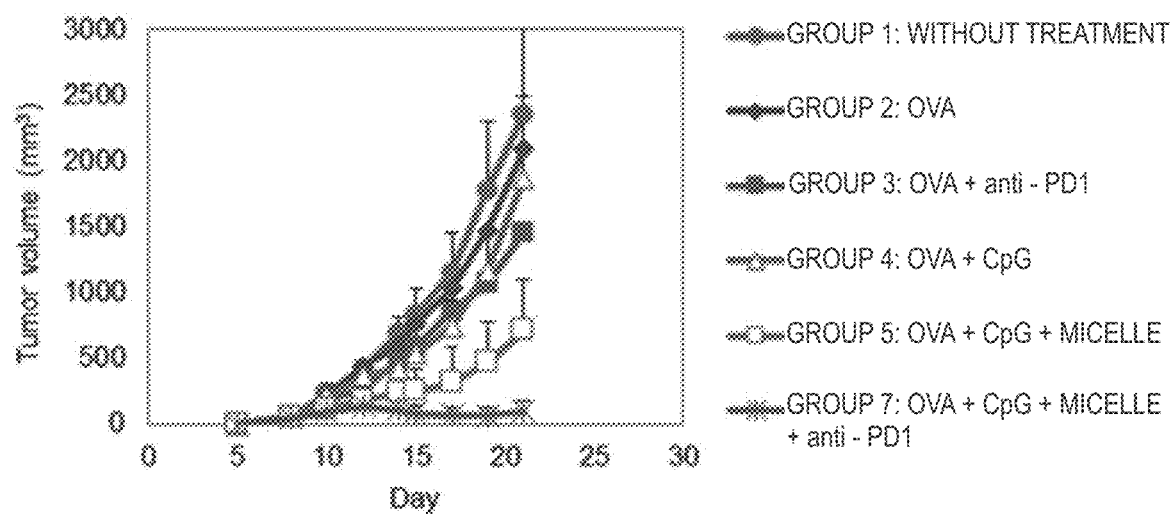
FIGS. 4(A) and 4(B) show the evaluation of the antitumor effect in a mouse tumor-bearing experimental system.
Figure 4B:
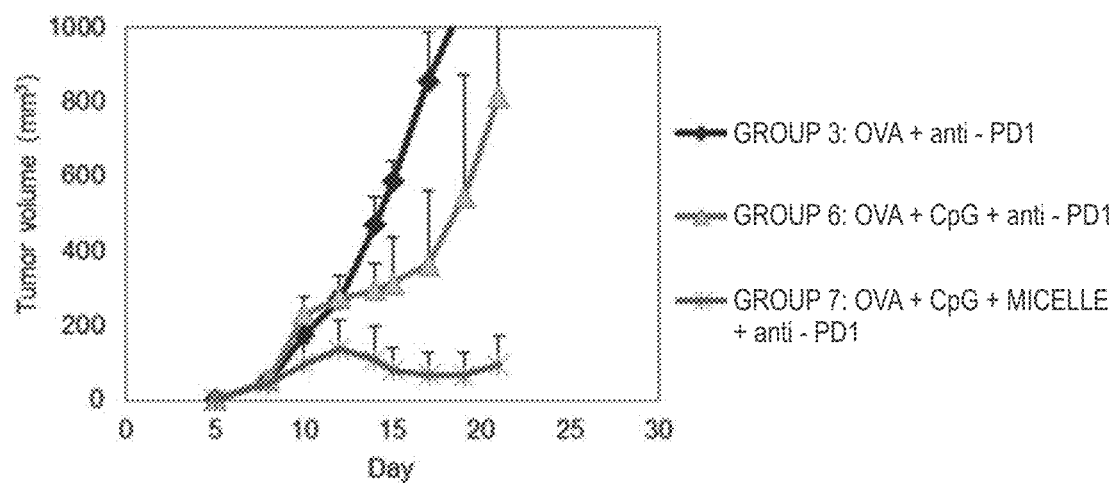

The obtained results are shown in FIGS. 4(A) and 4(B). The results were represented by an average value of the tumor sizes+standard deviation (SEM) (n=5).

FIG. 4(A) shows the results of Groups 1 to 5 and 7.

As compared to OVA alone (FIG. 4(A): Group 2) or the mixture of OVA and CpG-ODN (FIG. 4(A): Group 4), in the group administered with the mixture of OVA, CpG-ODN, and the pH sensitive carrier (FIG. 4(A): Group 5), an increase rate of tumors could be decreased to be low. It is considered that the mixture of OVA, CpG-ODN, and the pH sensitive carrier could induce a lot of CTLs having a function of attacking tumors in the living body as shown in FIG. 3(B), so that an increase in tumors could be delayed. Thus, it is shown that by containing the vaccine composition which contains OVA, CpG-ODN, and the pH sensitive carrier, a high antitumor effect is exhibited.

On the other hand, in the present experimental system, since an increase rate of tumors is fast, in the group administered with OVA and the anti-PD-1 antibody (FIG. 4(B): Group 3), a remarkable antitumor effect was not obtainable. Incidentally, in consideration of the action mechanism, which exhibits the antitumor effect, of the anti-PD-1 antibody, since the anti-PD-1 antibody does not have an ability to mature dendritic cells, even if a combination of the anti-PD-1 antibody and the pH sensitive carrier is used, it is assumed that CTL is not generated and enhancement in antitumor effect is not expected.

As compared to the mixture of OVA, CpG-ODN, and the pH sensitive carrier (FIG. 4(A): Group 5), the group further administered with the anti-PD-1 antibody (FIG. 4(A): Group 7) suppressed more significantly an increase in tumors. Some of individuals reached loss of tumors and this group had a particularly high antitumor effect. In the anti-PD-1 antibody alone (FIG. 4(A): Group 3), in view that a remarkable antitumor effect was not obtainable, a significant decrease in tumors by the combination use is a surprising result. It was shown that, even in the case of such a dosage amount of the anti-PD-1 antibody alone that does not exhibit the antitumor effect, the combination use of the vaccine composition containing OVA, CpG-ODN, and the pH sensitive carrier and the anti-PD-1 antibody results in a strong antitumor effect. Thus, it can be said that synergisticaction of the combination use of the vaccine composition containing OVA, CpG-ODN, and the pH sensitive carrier and the anti-PD-1 antibody results in a strong antitumor effect. It is considered that, since the anti-PD-1 antibody lowers the immunological escape ability of tumors, a lot of CTLs induced by the adjuvant composition can attack tumors so that a particularly high antitumor effect is obtainable.

Further, in the same experimental system, the combination use effect of the adjuvant composition and the immune checkpoint inhibitor was confirmed.

Figures 5A, 5B, 5C:
FIGS. 5(A)-5(C) show states of tumors of respective group mice after Day 21 from the cancer cell inoculation.

In order to verify the combination use effect of the adjuvant composition and the immune checkpoint inhibitor, comparison was performed in more detail. The results are shown in FIG. 4(B). In the combination use of the anti-PD-1 antibody and the natural immunity-activating substance (FIG. 4(B): Group 6), an increase rate of tumors from Day 10 was decreased and the antitumor effect could be confirmed; however, on Day 20, the tumor volume was increased again so that only a small effect was exhibited as compared to the combination use of the anti-PD-1 antibody and the adjuvant composition (FIG. 4(B): Group 7). The reason for this is considered that by using the natural immunity-activating substance alone, only a small amount of CTL could be induced and a large antitumor effect was not obtainable. Incidentally, FIGS. 5(A) to 5(C) show states of tumors of respective group mice. FIG. 5(A) shows mice of Group 3, FIG. 5(B) shows mice of Group 6, and FIG. 5(C) shows mice of Group 7. Also from the photographs of FIGS. 5(A)-5(C), it is found that the combination use of the adjuvant composition and the anti-PD-1 antibody exhibited an extremely high antitumor effect.

From the foregoing, in the combination use with the anti-PD-1 antibody, the adjuvant composition of the present invention exhibited most favorable combination use effect.

It was confirmed that the adjuvant composition containing the natural immunity-activating substance and the micelle of the pH sensitive carrier can induce a lot of CTLs so that the adjuvant composition has a larger combination use effect than the immune checkpoint inhibitor and can realize a particularly high antitumor effect. The combination of the adjuvant composition and the immune checkpoint inhibitor has favorable compatibility and is expected to contribute to the realization of a highly effective cancer immunotherapy.

The present application is based on Japanese Patent Application No. 2017-066142 filed on Mar. 29, 2017, the entire content of which is incorporated herein by reference.

REFERENCE SIGNS LIST

1: Amphipathic substance
2: pH sensitive compound
3: Natural immunity-activating substance
4: Adjuvant composition
5: Antigen
6: Vaccine composition
7: pH sensitive carrier
8: Dendritic cell
9: Endosome

The invention claimed is:

1. A composition comprising a pH sensitive carrier, a natural immunity-activating substance, and an immune checkpoint inhibitor,
    wherein the pH sensitive carrier comprises a pH sensitive compound and an amphipathic substance,
    wherein the pH sensitive compound is deoxycholic acid or a sodium salt thereof,
    wherein the amphipathic substance is 1,2-dilauroyl-sn-glycero-3-phosphatidylcholine,
    wherein the natural immunity-activating substance is an oligonucleotide comprising a CpG motif, and
    wherein the immune checkpoint inhibitor is anti-PD-1 antibody.

2. A composition comprising the composition according to claim 1 and an antigen.

3. A drug kit with a combination of an adjuvant composition, which contains a pH sensitive carrier and a natural immunity-activating substance, and an immune checkpoint inhibitor,
    wherein the pH sensitive carrier comprises a pH sensitive compound and an amphipathic sub stance,
    wherein the pH sensitive compound is deoxycholic acid or a sodium salt thereof,
    wherein the amphipathic sub stance is 1,2-dilauroyl-sn-glycero-3-phosphatidylcholine,
    wherein the natural immunity-activating substance is an oligonucleotide comprising a CpG motif, and
    wherein the immune checkpoint inhibitor is anti-PD-1 antibody.

4. The drug kit according to claim 3, wherein the drug kit is a drug kit for the treatment of cancer.

* * * * *